(12) United States Patent
Tennenbaum et al.

(10) Patent No.: US 9,393,284 B2
(45) Date of Patent: Jul. 19, 2016

(54) VISFATIN THERAPEUTIC AGENTS FOR THE TREATMENT OF ACNE AND OTHER CONDITIONS

(71) Applicant: ARAVA BIO-TECH LTD., Netanya (IL)

(72) Inventors: Tamar Tennenbaum, Jerusalem (IL); Liora Braiman-Wiksman, Rishon LeZion (IL); Revital Mandil-Levin, Ness Ziona (IL)

(73) Assignee: ARAVA BIO-TECH LTD., Netanya (IL)

( * ) Notice: Subject to any disclaimer, the term of this patent is extended or adjusted under 35 U.S.C. 154(b) by 0 days.

(21) Appl. No.: 14/474,142

(22) Filed: Aug. 31, 2014

(65) Prior Publication Data
US 2015/0065432 A1 Mar. 5, 2015

Related U.S. Application Data

(63) Continuation of application No. 12/652,798, filed on Jan. 6, 2010, now abandoned.

(60) Provisional application No. 61/208,386, filed on Feb. 24, 2009, provisional application No. 61/261,453, filed on Nov. 16, 2009.

(51) Int. Cl.
| | | |
|---|---|---|
| *A61K 38/16* | (2006.01) |
| *A61K 8/64* | (2006.01) |
| *A61K 8/92* | (2006.01) |
| *A61K 9/00* | (2006.01) |
| *A61K 9/06* | (2006.01) |
| *A61K 31/7052* | (2006.01) |
| *A61K 38/45* | (2006.01) |
| *A61Q 19/00* | (2006.01) |
| *C12N 15/113* | (2010.01) |
| *A61K 31/18* | (2006.01) |
| *A61K 31/4545* | (2006.01) |

(52) U.S. Cl.
CPC . *A61K 38/16* (2013.01); *A61K 8/64* (2013.01); *A61K 8/922* (2013.01); *A61K 8/925* (2013.01); *A61K 9/0014* (2013.01); *A61K 9/06* (2013.01); *A61K 31/18* (2013.01); *A61K 31/4545* (2013.01); *A61K 31/7052* (2013.01); *A61K 38/45* (2013.01); *A61Q 19/008* (2013.01); *C12N 15/113* (2013.01); *C12N 15/1137* (2013.01); *C12Y 204/02012* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 2006/0258562 A1* | 11/2006 | Tennenbaum | ......... | A61K 38/02 514/44 R |
| 2011/0269817 A1* | 11/2011 | Sassone-Corsi | ....... | A61K 31/00 514/44 A |
| 2012/0010172 A1* | 1/2012 | Christensen | ......... | C07D 213/40 514/90 |

* cited by examiner

*Primary Examiner* — Jennifer Pitrak McDonald
(74) *Attorney, Agent, or Firm* — Pearl Cohen Zedek Latzer Baratz LLP

(57) ABSTRACT

The present disclosure relates to compositions and methods for treating acne and other conditions. In particular, the compositions and methods are useful for the treatment of sebum associated conditions.

4 Claims, 7 Drawing Sheets

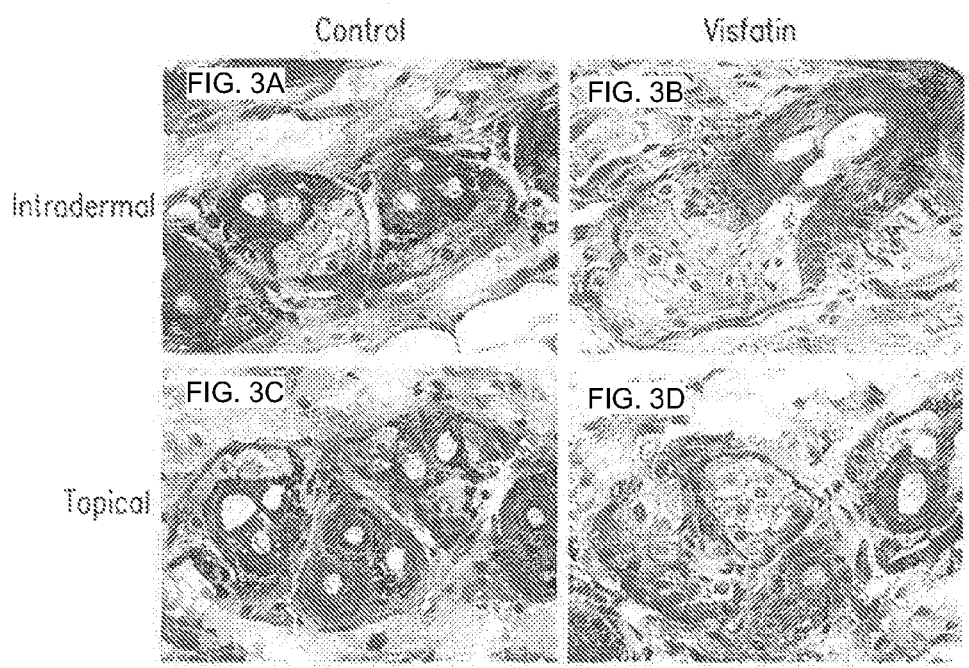

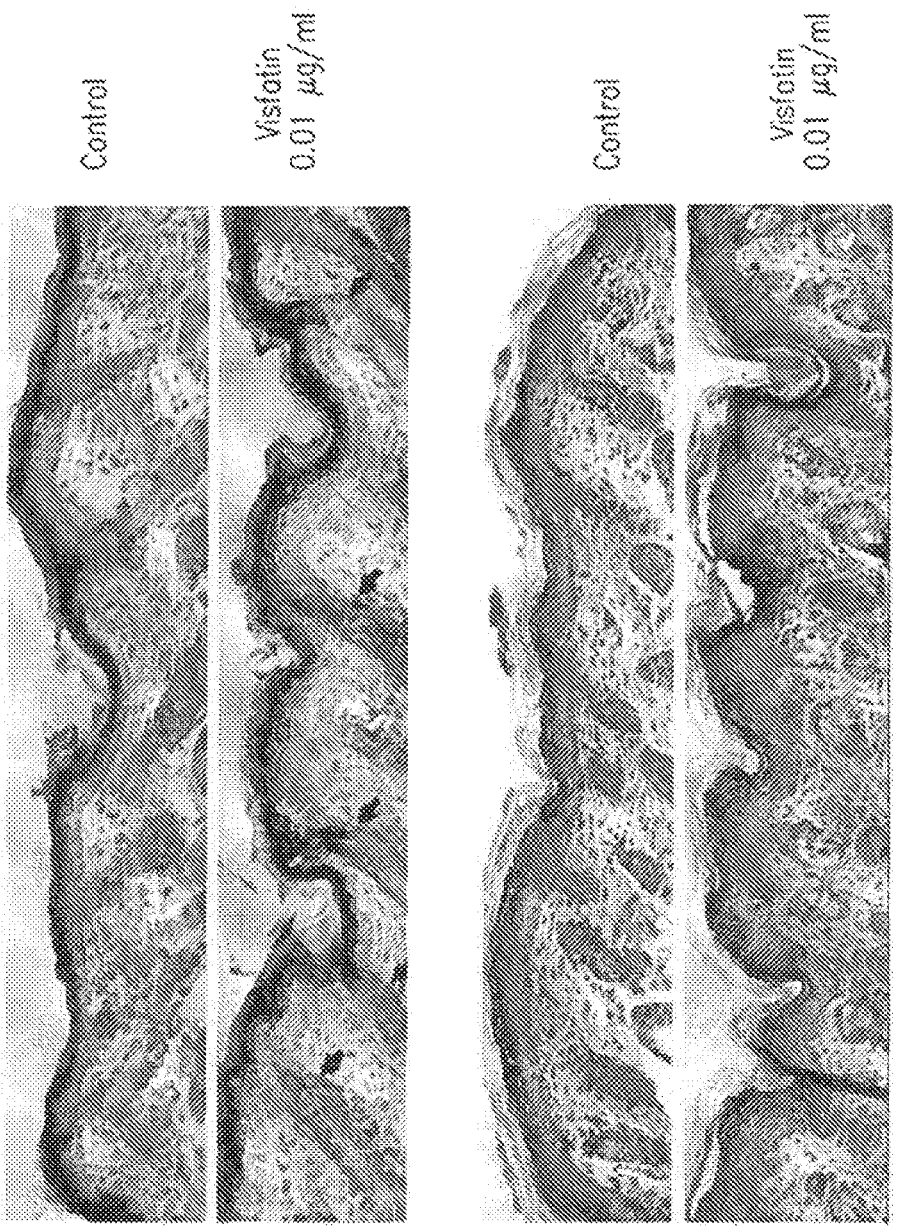

VISFATIN THERAPEUTIC AGENTS FOR THE TREATMENT OF ACNE AND OTHER CONDITIONS

PRIORITY

This application is a continuation of U.S. patent application Ser. No. 12/652,798, filed Jan. 6, 2010, which claims priority from U.S. Provisional Patent Applications Nos. 61/208,386 filed on Feb. 24, 2009 and 61/261,453 filed Nov. 16, 2009, all of which are hereby incorporated by reference.

FIELD OF THE DISCLOSURE

The present disclosure relates to compositions and methods for treating acne and other conditions such as dry or oily skin, associated with altered skin sebum levels.

BACKGROUND

Acne vulgaris one of the most treated skin condition in the United States and other countries. Acne vulgaris is a commonly referred to simply as "acne" even though many other different and clinically distinct forms of acne are know. Acne affects many adolescents and adults.

The earliest evidence of acne is usually the formation of a sebaceous plug in the pores of hair follicles present in an individual's skin. Typically, sebaceous plugs are very small and not visible to the unassisted eye. A sebaceous plug may be formed when a combination of dead keratinocyte cells from the upper cornified layers of the skin and sebum block the opening of these skin pores. Bacteria such as *Propionibacterium acnes* (*P. acnes*) can then proliferate in skin pores occupied by a sebaceous plug. Meanwhile, the resulting plug of cells and sebum may adhere to the walls of the skin pore leading to the formation of an even larger plug in the pore and the subsequent widening of the pore. These enlarged plugs are called comedones and are commonly referred to as "blackheads" or "whiteheads." Eventually, this enlargement can lead to the rupture of the pore walls and an inflammatory response. Once such a rupture has occurred, the body attempts to repair the skin and encapsulate the site of the inflammatory response by stimulating the growth of sheaths of cells out from the epidermis. However, the resulting encapsulation is often incomplete and may instead cause further rupture of the lesions that have been produced. This, in turn, can lead to the formation of multichanneled tracts as well as inflamed papules and inflamed pustules. These inflamed papules and inflamed pustules are commonly referred to as "pimples."

Acne can produce scarring and is regarded as unesthetic and unattractive. As a result, the other effects of acne are often psychological, such as reduced self-esteem. To complicate matters, acne usually appears during adolescence, when many individuals already tend to be very socially insecure. Early and aggressive treatment is, therefore, advocated to lessen the physical and psychological impact of acne on individuals.

There are four main strategies for treating acne. These four treatment strategies are directed to one, or more, aspects of acne. One strategy is to correct an altered pattern of follicular keratinization that occurs during acne. A second strategy is to decrease sebaceous gland activity and sebum production. A third strategy is to decrease the size of the follicular bacterial population and, in particular, to decrease the number of *P. acnes* bacteria. A fourth strategy is to inhibit the production, or effects, of extracellular inflammatory mediators (such as cytokines inflammatory cells) to produce an anti-inflammatory effect. Importantly, the majority of these treatment strategies suffer from limited efficacy or undesirable side effects.

Several categories of compositions have been used to implement these different acne treatment strategies. Isotretinoin and vitamin A derivatives represent one such category of compositions. Isotretinoin reduces sebaceous gland size by decreasing the proliferation of basal sebocytes, decreasing sebum production by up to 90% and inhibiting sebocyte differentiation. Isotretinoin is available in dosage forms suitable for either topical or oral administration. Oral administration of isotretinoin has revolutionized the treatment of severe acne. This is because isotretinoin is the first drug able to alter follicular keratinization, alter sebum production, decrease the follicular bacteria population and produce anti-inflammatory effects. Unfortunately, isotretinoin is a known teratogen and can cause birth defects. A number of other serious side effects are also associated with isotretinoin treatment. These side effects include psychiatric disorders, such as depression and psychosis, as well as intracranial hypertension, acute pancreatitis, increased blood lipid levels, hearing impairment, neurotoxicity and inflammatory bowel disease.

Benzoyl peroxide and related compounds represents a second category of compositions used to treat acne. Benzoyl peroxide is one of the most commonly used agents for the treatment of topical acne. Benzoyl peroxide has strong anti-microbial properties, weak anti-inflammatory properties and weak anti-comedone properties. Benzoyl peroxide for acne treatment is provided in dosage forms such as creams, gels, foams, soaps or washes for topical application. These formulations typically contain from 2.5% to 10% benzoylperoxide. However, a number of side effects are also associated with benzoyl peroxide treatment including contact sensitivities such as burning, itching, peeling and swelling of the skin.

Anti-androgens and related compounds represent a third category of compositions used to treat acne. Androgens are steroidal sex hormones such as testosterone associated with the development of male characteristics. Inocoterone acetate, spironolactone, cyproterone acetate, flutamide and 5-alpha reductase inhibitors, such as finasteride, are examples of anti-androgens used to treat acne. The female steroidal sex hormone estrogen is another example of and anti-androgen. Anti-androgens bind androgen receptors in the body and inhibit their biological activity or produce biological effects opposite to those of androgens (such as estrogen). Treatment with anti-androgens inhibits the production of sebum to help control acne. However, anti-androgen treatment by oral administration, or other routes, is typically restricted to female patients. This is because male patients receiving anti-androgens can develop female secondary characteristics such as breast enlargement and may suffer a loss of male secondary sex characteristics. This loss of male secondary sex characteristics can include the loss of muscle mass, reduced activity of the male organs and reduced sexual desire. Altogether, this means there are serious limitations and side-effects associated with anti-androgen based acne treatment.

Antibiotics and other anti-microbial compounds represent a fourth category of compositions used to treat acne. Examples of antibiotics used to treat acne include clindamycin and erythromycin which can be administered orally, or topically, to reduce the population of bacteria on skin surfaces and within the pores. Antibiotics can decrease the numbers of *P. acnes* bacteria and other bacteria to reduce the production of potentially pore clogging fatty acids, such as the propionic acid produced by *P. acnes* bacteria, on the skin surface. This means that antibiotics can have both an anti-comedogenic effect (such as preventing the formation of "blackheads" and "whiteheads") and can also help control the onset of inflammation resulting from the rupture of pore walls and the localized bacterial infection associated with this. However, a major limitation to the use of antibiotics to treat acne is an increase in the number of antibiotic resistant bacterial strains, including antibiotic resistant *P. acnes* strains, now in circulation.

As indicated above, sebum production plays a pivotal role in the pathogenesis of acne. Sebum production is known to promote the formation of comedones and increased sebum production is one of the early events that can contribute to the onset of acne.

Sebum is a mixture of relatively nonpolar lipids (such as oils, waxes and fats) which are mostly synthesized within the sebaceous glands. Secreted sebum provides a water-repellant, hydrophobic coating for the exterior surface of the skin. Thus, sebum normally helps lubricate and protect the skin.

Sebum is secreted by the sebaceous gland. The sebaceous glands are connected to hair follicles in the skin. The number of sebaceous glands in the skin remains approximately constant throughout the life of an individual, but the size of these glands tends to increase with age. Human sebaceous glands are a holocrine secreting tissues present in essentially all areas of the skin except for the palms and soles.

Holocrine secretions, such as sebum, result from the lysis of secretory cells in a gland. Holocrine secretions are first produced inside the secretory cells present in a gland. These secretory cells then rupture to release (secrete) the contents of these cells into the lumen, or interior space, of a gland.

In sebaceous glands, the cells responsible for the secretion of sebum are known as sebocytes. Sebocytes in the sebaceous gland fill with lipids and the other components of sebum. Sebocytes filled with these sebum components eventually lose their integrity and rupture. This causes the secretion of sebum by a sebaceous gland. Sebocytes filled with sebum have a characteristic, bubble-shaped cell morphology.

An increase in sebum secretion occurs in many people starting at about 9 years of age and continues to increase up to 17 years of age at which point the adult level of sebum secretion is typically reached. This period of increased sebum production is when most cases of acne occur. However, as discussed above, many of the strategies used to treat acne and control sebum production have undesirable side effects or other significant limitations. Sebum production also plays an important role in other conditions such as seborrhea (an abnormally increased secretion and discharge of sebum) as well as conditions in which dry and chapped skin develop.

Visfatin is an adipokine which is secreted by mature adipocytes. Visfatin is also called pre-B cell colony enhancing factor (PBEF), Nampt and nicotinamide phosphoribosyl transferase. Visfatin was initially reported as being secreted from visceral fat and was later reported to be secreted from subcutaneous adipocytes of the hypodermis. The hypodermis is a fat containing tissue located below the skin. The hypodermis also contains blood vessels and the basal (bottom) portion of hair follicles. Visfatin is also expressed by cells such as neutrophils and in tissues such as the liver, heart and muscle.

Visfatin is thought to be a visceral fat-derived hormone and has been reported by a Japanese group to mimic the biological activity of insulin both in vitro (~in glass) on cultured cells and in vivo (~in the living) by lowering plasma glucose levels in mice. However, this Japanese group later retracted their entire paper reporting these findings from the journal *Science*. The physiological role of visfatin is also unclear because the visfatin plasm concentration is 40-100 fold lower than that of insulin. Visfatin has also been reported to have enzymatic activity and can catalyzes the condensation of nicotinamide with 5-phosphoribosyl-1-pyrophosphate to yield nicotinamide mononucleotide. Importantly, the synthesis of nicotinamide mononucleotide is one step in the biosynthesis of the coenzyme nicotinamide adenine dinucleotide (NAD+).

This means the biological activities of visfatin and its role in physiological processes, such as the pathogenesis of acne and other conditions related to sebum production, are poorly understood. Importantly, visfatin may play a role in the pathogenesis of acne and other conditions, such as dry or oily skin, related to sebum production.

Thus, there is a need for improved compositions and methods that modulate visfatin activity to help treat acne and other conditions related to sebum production.

SUMMARY OF THE DISCLOSURE

One aspect of the disclosure is a pharmaceutical composition comprising a visfatin active agent and a pharmaceutically acceptable carrier. Such pharmaceutically acceptable carriers can comprise diluents or adjuvants. In a preferred embodiment, a delivery peptide is used either with, or without, the pharmaceutically acceptable carrier but in combination with the visfatin active agent.

Another aspect of the disclosure is a method of treating a sebum over-production condition in a subject comprising administrating a therapeutically effective amount of a visfatin antagonist, or a pharmaceutical composition containing a visfatin antagonist, to a subject with a sebum over-production condition; whereby the sebum over-production condition is treated.

Another aspect of the disclosure is a method of treating acne vulgaris in a subject comprising administering a therapeutically effective amount of a visfatin antagonist, or a pharmaceutical composition containing a visfatin antagonist, to a subject with acne vulgaris; whereby the acne vulgaris is treated.

Another aspect of the disclosure is a method of treating a sebum production deficiency condition in a subject comprising administering a therapeutically effective amount of a visfatin agonist, or a pharmaceutical composition containing a visfatin agonist, to a subject with a sebum production deficiency condition; whereby the sebum production deficiency condition is treated.

Another aspect of the disclosure is a method of increasing the sebum production of a subject comprising administering a therapeutically effective amount of a visfatin agonist composition, or a pharmaceutical composition containing a visfatin agonist, to the skin of a subject; whereby the sebum production of the subject is increased.

Another aspect of the disclosure is s method of decreasing the sebum production of a subject comprising administering a therapeutically effective amount of a visfatin antagonist composition, or a pharmaceutical composition containing a visfatin antagonist, to the skin of the subject, whereby the sebum production of the subject is decreased.

Another aspect of the disclosure is the use of an siRNA comprising a nucleic acid sequence selected front the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 9, SEQ ID NO: 10, SEQ ID NO: 13, SEQ ID NO: 14, SEQ ID NO: 17, and SEQ ID NO: 18 in the manufacture of a medicament for the treatment of a sebum-overproduction condition.

Another aspect of the disclosure is the use of an siRNA comprising a nucleic acid sequence selected from the group consisting of SEQ ID NO: 19, SEQ ID NO: 20, SEQ ID NO:

21, SEQ ID NO: 22, SEQ ID NO: 23, SEQ ID NO: 24, SEQ ID NO: 25, SEQ ID NO: 26, SEQ ID NO: 9, SEQ ID NO: 10, SEQ ID NO: 13, SEQ ID NO: 14, SEQ ID NO: 17, and SEQ ID NO: 18 in the manufacture of a medicament for the treatment of a condition selected from the group consisting of acne, seborrhea seborrhoeic dermatitis, a sebaceous cyst and sebaceous hyperplasia.

Another aspect of the disclosure is the use of FK-866 in the manufacture of a medicament for the treatment of a sebum-overproduction condition.

Another aspect of the disclosure is the use of FK-866 in the manufacture of a medicament for the treatment of a condition selected from the group consisting of acne, seborrhea, seborrhoeic dermatitis, a sebaceous cyst and sebaceous hyperplasia.

Another aspect of the disclosure is the use of APO866 in the manufacture of a medicament for the treatment of a sebum-overproduction condition.

Another aspect of the disclosure is the use of APO866 in the manufacture of a medicament for the treatment of a condition selected from the group consisting of acne, seborrhea, seborrhoeic dermatitis, a sebaceous cyst and sebaceous hyperplasia.

Another aspect of the disclosure is the use of an siRNA comprising a nucleic acid sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 9, SEQ ID NO: 10, SEQ ID NO: 13, SEQ ID NO: 14, SEQ ID NO: 17, and SEQ ID NO: 18 in the manufacture of a medicament for the treatment of acne vulgaris.

Another aspect of the disclosure is the use of a visfatin agonist comprising at least one amino acid sequence selected from the group consisting of SEQ ID NO: 2, SEQ ID NO: 4, SEQ ID NO: 6 and SEQ ID NO: 8 in the manufacture of a medicament for the treatment of a sebum production deficiency condition.

Another aspect of the disclosure is the use of a visfatin agonist comprising at least one amino acid sequence selected from the group consisting of SEQ ID NO: 2, SEQ ID NO: 4, SEQ ID NO: 6 and SEQ ID NO: 8 in the manufacture of a medicament for the treatment of xerosis condition associated with at least one selected from the group consisting of chapping, dermatitis, psoriasis, diabetes, renal failure, renal transplantation, hemodialysis, vitamin A deficiency and angular cheilitis.

Another aspect of the disclosure is a pharmaceutical composition adapted for treating a sebum over-production condition in a subject comprising administering a therapeutically effective amount of a visfatin antagonist to a subject with a sebum over-production condition; whereby the sebum over-production condition is treated.

Another aspect of the disclosure is a pharmaceutical composition adapted for treating acne vulgaris in a subject comprising administering a therapeutically effective amount of a visfatin antagonist to a subject with acne vulgaris; whereby the acne vulgaris is treated.

Another aspect of the disclosure is a pharmaceutical composition adapted for treating a sebum production deficiency condition in a subject comprising administering a therapeutically elective amount of a visfatin agonist to a subject with a sebum production deficiency condition; whereby the sebum production deficiency condition is treated.

Another aspect of the disclosure is a pharmaceutical composition adapted for increasing the sebum production of a subject comprising administering a therapeutically effective amount of a visfatin agonist to the skin of a subject; whereby the sebum production of the subject is increased.

Another aspect of the disclosure is a pharmaceutical composition adapted for decreasing the sebum production of a subject comprising administering a therapeutically effective amount of a visfatin antagonist to the skin of the subject, whereby the sebum production of the subject is decreased.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 3A-3E show that visfatin increases the number of bubbled shaped, sebocyte cells in sebaceous glands.

FIGS. 4A-4D show that topical treatment with visfatin induces maturation and lipid accumulation in the sebaceous glands.

FIGS. 5A-5F show that topical treatment with a visfatin antagonist siRNA suppresses sebum production in the sebaceous glands.

DETAILED DESCRIPTION OF THE DISCLOSURE

Figure 1A:
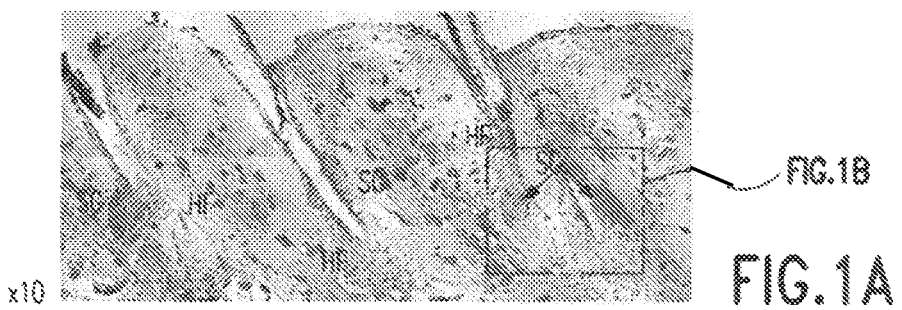
FIGS. 1A-1B show that visfatin expression is restricted to the sebaceous glands.

It will be appreciated that the following description is intended to provide details concerning specific representative aspects of the disclosure. It will also be appreciated that a wide variety of equivalents may be substituted for the specified elements of the methods described herein without departing from the spirit and scope of this disclosure as described in the appended claims. Additionally, all publications, including but not limited to patents and patent applications, cited in this disclosure are herein incorporated by reference as though fully set forth. Ranges identified herein are intended to include the values defining the upper and lower limits of a recited range, all discrete values within the range and any discrete sub-range within the range.

The term "visfatin active agent" as used herein includes without limitation any molecule that positively or negatively modulates, by any mechanism, the activity of a visfatin protein either directly or indirectly. Examples of such visfatin active agents include, for example, both visfatin agonist and visfatin antagonists molecules such as those described herein.

The term "visfatin agonist" as used herein includes without limitation a molecule that partially or completely increases, by any mechanism, the activity of a visfatin protein. A visfatin agonist may be a molecule that is capable of, directly or indirectly, substantially increasing or stimulating visfatin mediated signal transduction. A visfatin agonist may also be a molecule that is capable of, directly or indirectly, substantially increasing or stimulating an enzymatic activity of a visfatin protein such as the catalyzing the condensation of nicotinamide with 5-phosphoribosyl-1-pyrophosphate to yield nicotinamide mononucleotide. For example, a visfatin agonist may increase the activity of a visfatin protein comprising the amino acid sequences shown in SEQ ID NO: 2, SEQ ID NO: 4, SEQ ID NO: 6 or SEQ ID NO: 7, or homologs of these, produced by cells. In particular, a visfatin agonist may increase the visfatin activity in the cells, or tissues, of a subject (skin) when the number of visfatin protein molecules present in the cell, or tissues, are increased relative to some initial state. Thus, a visfatin agonist can comprise the amino acid sequences shown in SEQ ID NO: 2, SEQ ID NO: 4, SEQ ID NO: 6 or SEQ ID NO: 7, or homologs of these, which have been delivered to cells or a tissue.

Visfatin agonists may also operate by other mechanisms including, for example, gene activation through recombination to produce constitutively activated, or inducibly activated genomic or visfatin agonist coding DNAs (such as gene knock-in, promoter hijacking or other gene methods).

Visfatin agonists, such as compounds or molecules, useful in the methods of the disclosure may comprise, for example, small organic molecules, peptide chains (such as proteins), antibodies, antibody fragments, polynucleotides or combinations of these.

Agonists useful in the methods of the disclosure may also be nucleic acid molecules. Alternatively, polynucleotide molecules such as double and single stranded plasmid DNA vectors, artificial chromosomes, or linear nucleic acids or other vectors that encode a visfatin agonist (such as peptide chain), or function as a visfatin agonist, may be used in the methods of the disclosure to administer an agonist to a subject.

The term "visfatin antagonist" as used herein includes without limitation a molecule that partially or completely inhibits, by any mechanism, an activity of a visfatin protein. A visfatin antagonist may be a molecule that is capable of, directly or indirectly, substantially counteracting, reducing or inhibiting visfatin mediated signal transduction. A visfatin antagonist may also be a molecule that is capable of, directly or indirectly, substantially counteracting, reducing or inhibiting an enzymatic activity of a visfatin protein such as the catalyzing the condensation of nicotinamide with 5-phosphoribosyl-1-pyrophosphate to yield nicotinamide mononucleotide. For example, a visfatin antagonist may partially, or completely, inhibit the activity of a visfatin protein comprising the amino acid sequences shown in SEQ ID NO: 2, SEQ ID NO: 4, SEQ ID NO: 6 or SEQ ID NO: 7, or homologs of these, produced by cells.

Visfatin antagonists, such as compounds or molecules, useful in the methods of the disclosure may comprise, for example, small organic molecules, peptide chains, antibodies, antibody fragments, polynucleotides or combinations of these.

Importantly, a visfatin antagonist can inhibit the expression of a visfatin protein by, for example, RNA interference. Visfatin antagonists may also operate by other mechanisms include, for example, gene inactivation through recombination to inactivate genomic DNAs (such as gene knock-out, promoter hijacking or other gene mutagenesis methods) and gene transcript inactivation using anti-sense RNAs.

Antagonists useful in the methods of the disclosure may also be nucleic acid molecules. Such nucleic acid molecules may be interfering nucleic acid molecules such as short interfering RNAs or antiserum molecules that are antagonists of an activity of visfatin. Alternatively, polynucleotide molecules such as double and single stranded plasmid DNA vectors, artificial chromosomes, or linear nucleic acids or other vectors that encode an antagonist (such as peptide chain or RNA), or function as an antagonist, may be used in the methods of the disclosure to administer an antagonist to a subject.

Visfatin active agent may also be referred to as visfatin modulating agents.

The term "delivery peptide" as used herein includes without limitation a peptide chain that delivers, or increases the delivery of, an active agent to a tissue in a patient on the administration of a composition containing the active agent and the delivery peptide. Delivery of an active agent to a tissue in a patient can be assessed by comparison of the amount, or magnitude of the biological effects of, an active agent present in a tissue when a composition containing a active agent and a delivery peptide is administered to a tissue is a patient and the amount of active agent, or the magnitude of its effects, when a composition that contains the active agent but does not contain the delivery peptide is administered. Delivery peptides may be, for example, cationic, lipophilic peptide chains. Such peptide chains may comprise side chain groups that have a positive charge at a particular pH or are coupled to chemical groups or compositions (such as ion exchange resins) which have a positive charge under particular conditions. Such peptide chains may also comprise a lipophilic portion, or chemical group, that is hydrophobic in character. Such lipophilic portions may be covalently attached lipid groups such as fats, waxes, sterols including fatty acids, triglycerols, cholesterols, fat soluble vitamins and the like. One example of such a cationic, lipophilic peptide chain is an amino terminally myristoylated peptide having the amino acid sequence shown in SEQ ID NO: 27. A delivery peptide may also form micelles or other structures that results in delivery, or increases the delivery of, an active agent to a tissue in a patient. A delivery peptide may also be a carrier, that can be chemically coupled to an active agent or mechanically associated with an active agent (such as by encapsulation), to deliver an active agent to a tissue in a patient. Such delivery peptides which are carriers may comprise organelle targeting signals, molecules that are endocytosed and the like.

The term "siRNA" as used herein includes without limitation a short interfering nucleic acid sequence that mediates the cleavage of a target gene transcript. Short interfering RNAs (siRNAs) may be double stranded or of the short hairpin type. Double stranded siRNAs may be comprised of two individual, antiparallel, annealed RNA strands or annealed nucleic acid strands which contain both RNA and DNA (such as 5'-ttttuuuu-3' annealed to 5'-ttttuuuu-3' or 5'-tttt-3' annealed to 5'-uuuu-3'). Typically, double stranded siRNAs contain two separate nucleic acid strands of 18 to 21 nucleotides which are hybridized to each other and have 16 to 19 RNA nucleotides located at the 5' terminus of each strand and two "tt" DNA nucleotides located at the 3' terminus of each strand. siRNAs of the short hairpin type may be comprised of a single RNA strand or a single RNA:DNA hybrid strand capable of forming a stem-and-loop structure or other secondary structure effective as an siRNA. Those skilled in the art will recognize that siRNAs may comprise other modifications such as nucleoside analogs, backbone modifications, and other modifications that still permit the modified siRNA nucleic acid to mediate the cleavage of a target gene transcript.

The term "sebum over-production condition" as used herein includes without limitation a condition in which a large amount of sebum is produced by a subject which results in a pathological condition or undesirable condition. Examples of such sebum over-production conditions include acne, seborrhea, seborrhoeic dermatitis, a sebaceous cyst and sebaceous hyperplasia and related conditions. In the case of acne such related conditions may include, for example, acne vulgaris, acne artificialis, bromide acne, acne cachecticorum, acne ciliaris, acne cosmetica, cystic acne, acne fulminans, acne generalis, halogen acne, acne hypertrophica, iodide acne, acne medicamentosa, acne nonatorum, pomade acne, acne punctata, acne pustulosa, acne rosacea, steroid acne, chloracne, tropic acne, acne varioliforms and acne urticata.

The term "subject" as used herein includes without limitation an animal belonging to any genus for which treatment of a sebum over-production condition, sebum production deficiency condition, an increase in sebum production or a decrease in sebum production is indicated. One example of such a subject is a human such as a human patient.

The term "administering" as used herein includes without limitation providing a composition to at least one tissue, such as the skin, of a subject. Such compositions may be administered to a subject corporeally or extra-corporeally. Extra-corporeal administration of a composition to a tissue of a subject occurs when a portion of a tissue, such as blood or bone marrow, is removed from the body of a subject, contacted with a composition that has been provided and a portion of the tissue contacted with the composition is then returned to body of a subject. Topical administration and intradermal administration are forms of corporeal administration.

The term "therapeutically effective amount" as used herein includes without limitation those doses of a composition that, in a given individual subject, produce a response that results in improvement, or treatment, of one or more symptoms of a sebum over-production condition, sebum production deficiency condition, an increase in sebum production or a decrease in sebum production in a subject. For example, a therapeutically effective amount of a composition may be a dose of an active agent, such as a visfatin active agent, that improves or treats the symptoms of an acne such as acne vulgaris. Therapeutically effective amounts, or doses, appropriate for an individual subject can be readily determined using routine clinical techniques well known by those of skill in the art (such as dose response plots). Such doses may include, for example, from $1 \times 10^{-12}$ g to 100 g of a visfatin agonist, or a visfation antagonist, per kg of the body weight of a subject.

One of ordinary skill in the art can determine an effective amount of a composition by histology, H & E staining, keratin 14 staining, or immunochemistry or by observing abscess formation and other by routine experimentation easily performed by one of ordinary skill in the art.

One of skill in the art can also confirm that an effective amount of a composition has been administered to a subject with a condition by simply observing or measuring the change in an area affected by the condition before treatment and a reasonable time after treatment. The compositions of the disclosure can comprise therapeutically effective amounts of the components of these compositions.

In the methods of the disclosure a therapeutically effective amount of the active agent (such as a visfatin active agent), or a pharmaceutical composition containing it is administered to a subject in need thereof. The composition can be administered by topical application in a solution, ointment, gel, cream or any local application (such as subcutaneous injection). The active agent may be in the form of a pharmaceutical composition and may also be administered by way of a drug eluting device, such as gauze, a patch, pad, or a sponge.

Compositions should be administered as frequently as necessary and for as long of a time as necessary to treat a sebum over-production condition, sebum production deficiency condition, or to cause an increase in sebum production or a decrease in sebum production in a subject, as indicated, to achieve the desired endpoint, for example, until the condition, such as acne, completely resolves. One of ordinary skill in the art can readily determine a suitable course of treatment utilizing the compositions and methods according to this disclosure.

The term "sebum production deficiency condition" as used herein includes without limitation a condition in which a low amount of sebum is produced by a subject which results in a pathological condition or undesirable condition. Examples of such sebum production deficiency condition include xerosis (~dry skin) conditions associated with chapping, dermatitis, psoriasis, diabetes, renal failure, renal transplantation, hemodialysis, vitamin A deficiency and angular cheilitis.

The term "drug eluting scaffold" as used herein, includes without limitation a stationary material capable of releasing a physiologically active molecule. Drug eluting scaffolds may comprise stationary phase materials which may be insoluble, soluble, non-bioabsorbable, or bioabsorbable.

The term "homolog" as used herein includes without limitation protein sequences having between 85% and 100% sequence identity to a reference sequence. For example, homologs of the *Homo sapiens* visfatin protein shown in SEQ ID NO: 2 would include those proteins with an amino acid sequence having between 90% and 100% sequence identity to SEQ ID NO: 2. Percent identity between two proteins can be determined by pair wise alignment using the default settings of the AlignX module of Vector NTI v.9.0.0 (Invitrogen Corp., Carlsbad, Calif.)

The term "peptide chain" as used herein includes without limitation a molecule that comprises at least two amino acid residues linked by a peptide bond to form a chain. Large peptide chains of more than 50 amino acids may be referred to as "polypeptides" or "proteins." Small peptide chains less than 50 amino acids may be referred to as "peptides."

The term "pharmaceutically acceptable carrier" as used herein includes without limitation one or more compatible solid or liquid filler diluents or encapsulating substances which are suitable for administration to a human or other animal.

Examples of suitable pharmaceutically acceptable carriers include water, petroleum jelly, petrolatum, mineral oil, vegetable oil, animal oil, organic and inorganic waxes, such as microcrystalline, paraffin and ozocerite wax, natural polymers such as xanthanes, malt, talc, gelatin, sugars, cellulose, collagen, starch, or gum arabic, synthetic polymers, alcohols, polyols, phosphate buffer solutions, cocoa butter, emulsifiers, detergents such as the TWEENs™ and the like. The carrier may be a water miscible carrier composition that is substantially miscible in water such as, for example, alcohols. Water miscible topical pharmaceutically acceptable carriers can induce those made with one or more ingredients described above, and can also include sustained or delayed release carriers, including water containing, water dispensable or water soluble compositions, such as liposomes, microsponges, microspheres or microcapsules, aqueous base ointments, water-in-oil or oil-in-water emulsions, gels or the like. Those of ordinary skill in the art will recognize other pharmaceutically acceptable carriers.

Other compatible pharmaceutical actives and additives may be included in the pharmaceutically-acceptable carrier for use in the compositions of the disclosure. For example, drugs useful in the treatment of acne such as antibiotics, isotretinoin, vitamin A derivatives, benzoyl peroxides, and anti-androgens may be included in the compositions of the disclosure. Local anesthetics such as NOVOCAINE™, lidocaine, or others may also be included in the pharmaceutically acceptable carrier. Adjuvants may also be included in a pharmaceutically acceptable carrier. Additives such as benzyl alcohol and other preservatives can be included in the pharmaceutically acceptable carrier as well. Those of ordinary skill in the art will readily recognize other pharmaceutically acceptable actives and additives suitable for inclusion in the compositions of the disclosure.

A visfatin agonist may be recombinantly expressed. Recombinant expression by transformation of a host cell with recombinant DNA may be carried out by conventional techniques which are well known to those skilled in the art. The host cell may be a prokaryotic, archaeal, or eukaryotic cell. The isolation and purification of recombinantly expressed polypeptides such as recombinant visfatin proteins can carried out by techniques that are well known in the art including, for example, preparative chromatography and affinity purification using antibodies or other molecules that specifically bind a given polypeptide.

Such proteins can be synthesized by such commonly used methods as t-BOC or FMOC protection of alpha-amino groups. Both methods involve stepwise syntheses whereby a single amino acid is added at each step starting from the carboxy terminus of the peptide (Coligan et al., Current Protocols in Immunology, Wiley Interscience, 1991, Unit 9). Peptides of the disclosure can also be synthesized by the well known solid phase peptide synthesis methods described in Merrifield (85 J. Am. Chem. Soc. 2149 (1962)), and Stewart and Young, Solid Phase Peptides Synthesis, (Freeman, San Francisco, 1969, pp. 27-62), using a copoly(styrene-divinyl-benzene) containing 0.1-1.0 mMol amines/g polymer. On completion of chemical synthesis, the peptides can be deprotected and cleaved front the polymer by treatment with liquid HF-10% anisole for about ¼-1 hours at 0° C. After evaporation of the reagents, the peptides are extracted from the polymer with a 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, and solubility based methods.

Peptides can also be synthesized by any biological method, such as by recombinant expression of the protein in mammalian cells, insect cells, yeast and bacteria and cell free systems such as in vitro (~in glass) transcription and translation systems. Protein expression can be optimized for each system by well-established methods. Protein can be purified by standard methods (Frederich M. Ausubel, et al., Current Protocols to Molecular Biology, Wiley Interscience, 1989). For example, the protein can be expressed in bacteria as GST-fusion protein and purified by glutathione agarose beads (Sigma) as described (Erangionic and Neel, Analytical Biochemistry, 210:179, 1993). Alternatively, the protein can be expressed as a secretory product in mammalian cells and purified from conditioned medium (Cadena and Gill, Protein Expression and Purification 4:177, 1993). Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc. Natl. Acad. Sci., USA 82:5131 (1985). Peptides may also be synthesized by, using covalent modification, liquid-phase peptide synthesis, or any other method known to one of ordinary skill in the art.

Peptides can be synthesized using amino acids or amino acid analogs, the active groups of which are protected as necessary using, for example, a t-butyldicarbonate (t-BOC) group or a flourenylmethoxy carbonyl (FMOC) group. Amino acids and amino acids analogs can be purchased commercially (Sigma Chemical Co.; Advanced Chemtec) or synthesized using methods known in the art.

Amino acids in the peptides disclosed herein can be modified by amino acid substitution of one or more of the specific amino acids shown in the exemplified peptides. An amino acid substitution change can include the substitution of one basic amino acid for another basic amino acid, one hydrophobic amino acid for another hydrophobic amino acid or other conservative substitutions. Amino acid substitutions can also include the use of non-naturally occurring amino acids such as, for example, ornithine (Orn) or homoArginine (homoArg) for Arg.

Peptides can also be modified by the covalent attachment of other molecules or reaction of a functional group present in a peptide. Examples of such modifications include the attachment of polyethyleneglycol molecules, lipid, carbohydrate, or other molecules. A specific example of such a modification is myristoylation such as amino terminal myristoylation. Techniques for the covalent modification of peptides are well known in the art and those of ordinary skill will recognize a number of such techniques.

The term "standard state" as used herein includes without limitation a temperature of 25° C.+/−2° C. and a pressure of 1 atmosphere. The concentrations of the solutions, suspensions, and other preparations described herein and expressed on a per unit volume basis (such as mol/L, M, units/ml, μg/ml and the like) or on a percentage by weight relative to the total weight of a composition are determined at standard state. The term standard state is not used in the art to refer to a single art recognized set of temperatures or pressure, but is instead a reference state that specifies temperatures and pressure to be used to describe a solution, suspension, or other preparation with a particular composition under the reference standard state conditions. The volume of a solution may be, in part, a function of temperature and pressure. Those skilled in the art will recognize that compositions equivalent to those disclosed here can be produced at other temperatures and pressures.

Compositions suitable for administration in the methods of the disclosure may be provided in the form of solutions, ointments, emulsions, creams, gels, granules, films and plasters. Those of ordinary skill in the art will recognize other forms of the disclosed compositions suitable for administration to a subject.

One aspect of the disclosure is a composition comprising a visfatin active agent and a pharmaceutically acceptable carrier.

In one embodiment of the disclosure the composition further comprises a delivery peptide.

Another embodiment of the disclosure is a composition wherein the visfatin active agent is a visfatin agonist.

Another embodiment of disclosure is a composition comprising from about 0.001 to about 10% by weight of the visfatin agonist.

Another embodiment of the disclosure is a composition comprising about 1% by weight of the visfatin agonist, about 95% by weight water, about 0.2% by weight montan wax, about 0.2% by weight bee wax, about 0.2% by weight sorbitol, about 0.2% by weight shea butter, about 1% by weight borage oil, about 1% by weight calendula oil, about 0.2% by weight Hamamelis extract and about 0.1% by weight castor oil.

Another embodiment of the disclosure is a composition wherein the visfatin agonist comprises at least one amino acid sequence selected front the group consisting of SEQ ID NO: 2, SEQ ID NO: 4, SEQ ID NO: 6 and SEQ ID NO: 8.

Another embodiment of the disclosure is a composition wherein the visfatin agonist comprises the amino acid sequence of SEQ ID NO: 2.

Another embodiment of the disclosure is a composition which is a cream.

Another aspect of the disclosure is a composition wherein the visfatin active agent is a visfatin antagonist and the delivery peptide is an amino terminally myristoylated peptide having the amino acid sequence shown in SEQ ID NO: 27.

Another embodiment of the disclosure is a composition wherein the visfatin antagonist is at least one siRNA targeting a nucleic acid encoding a protein comprising a sequence selected from the group consisting of SEQ ID NO: 2, SEQ ID NO: 4, SEQ ID NO: 6 and SEQ ID NO: 8.

Importantly, such siRNAs can target a nucleic acid selected from the group consisting of SEQ ID NO: 1, SEQ ID NO: 3, SEQ ID NO: 5 and SEQ ID NO: 9.

Double stranded type siRNAs, including short hairpin type siRNAs, may be constructed using the following principles. In general, the sequence targeted by an siRNA is 21 nucleotides in length and should avoid regions within 50-100 base pairs of the start codon and the termination (stop) codon, avoid intron regions, avoid stretches of 4 or more bases (such as 5'-aaaa-3', 5'-cccc-3' and the like), avoid regions with GC content greater than 30% or less than 60%, avoid repeating sequences, avoid low complexity sequences, avoid single nucleotide polymorphism (SNP) sites. Candidate siRNAs targeting sequences satisfying these criteria can then be designed. A BLAST algorithm based homology search, such as a BLASTN algorithm based search, should then be conducted with candidate siRNAs to identify candidates with low, or now homology to other genes or sequences. This helps avoid off-target effects. A negative control RNA version of each candidate siRNA should be constructed in which the nucleic acid sequence of the candidate siRNA is scrambled. The negative control RNA should have the same length and nucleotide composition as the siRNA but have at least 4-5 bases mismatched to the siRNA. It may be confirmed by a BLAST algorithm based homology search that the negative control RNA does not have homology to other genes. The candidate siRNA, such as an siRNA which is a visfatin antagonist, can then be confirmed to be an siRNA in controlled assays if it decrease the levels of the targeted gene transcript either, in vivo (~in the living) or in vitro (~in glass), or the levels of a protein encoded by the targeted gene relative to the negative control RNA.

siRNAs can also be constructed according to the Dharmacon algorithm, Ambion algorithm or other similar algorithms for siRNA design which are well known by those of ordinary skill in the art. Such algorithms are readily accessible via the internet or commercially available software packages. Alternatively, siRNAs that have been previously identified may be used in use methods of the disclosure or included in the compositions of the disclosure.

Another embodiment of the disclosure is a composition comprising at least one siRNA selected from the group consisting of a first siRNA, a second siRNA, a third siRNA and a fourth siRNA; wherein the first siRNA is a double stranded nucleic acid comprising the sentences shown in SEQ ID NO: 19 and SEQ ID NO: 29, the second siRNA is a double stranded nucleic acid comprising the sequences shown in SEQ ID NO: 21 and SEQ ID NO: 22, the third siRNA is a double stranded nucleic acid comprising the sequences shown in SEQ ID NO: 23 and SEQ ID NO: 24, and the fourth siRNA is a double stranded nucleic acid comprising the sequences shows in SEQ ID NO: 25 and SEQ ID NO: 26.

Another embodiment of the disclosure is a composition comprising at least one siRNA selected from the group consisting of a first siRNA, a second siRNA and a third siRNA; wherein the first siRNA is a double stranded nucleic acid comprising the sequences shown in SEQ ID NO: 9 and SEQ ID NO: 10, the second siRNA is a double stranded nucleic acid comprising the sequences shown in SEQ ID NO: 13 and SEQ ID NO: 14, and the third siRNA is a double stranded nucleic acid comprising the sequences shown in SEQ ID NQ: 17 and SEQ ID NO: 18.

Another embodiment of the disclosure is a composition further comprising an aqueous carrier and DMSO.

Examples of such aqueous carriers include distilled water, buffered solutions such as PBS and gels comprising water.

Another aspect of the disclosure is a method of treating a sebum over-production condition in a subject comprising administering a therapeutically effective amount of a visfatin antagonist, or a pharmaceutical composition containing a visfatin antagonist, to a subject with a sebum over-production condition; whereby the sebum over-production condition is treated.

Another embodiment of the disclosure is a method wherein the sebum over-production condition is selected from the group consisting of acne, seborrhea, seborrhoeic dermatitis, a sebaceous cyst and sebaceous hyperplasia.

Other embodiments of the disclosure are methods wherein the visfatin antagonist comprises at least one siRNA targeting a nucleic acid encoding a protein comprising a sequence selected from the group consisting of SEQ ID NO: 2, SEQ ID NO: 4, SEQ ID NO: 6 and SEQ ID NO: 8.

Other embodiments of the disclosure are methods wherein the siRNA is at least one selected from the group consisting of a first siRNA, a second siRNA, a third siRNA and a fourth siRNA; wherein the first siRNA is a double stranded nucleic acid comprising the sequences shown in SEQ ID NO: 19 and SEQ ID NO: 20, the second siRNA is a double stranded nucleic acid comprising the sequences shown in SEQ ID NO: 21 and SEQ ID NO: 22, the third siRNA is a double stranded nucleic acid comprising the sequences shown in SEQ ID NO: 23 and SEQ ID NO: 24, and the fourth siRNA is a double stranded nucleic acid comprising the sequences shown in SEQ ID NO: 25 and SEQ ID NO: 26.

Other embodiments of the disclosure are methods wherein the siRNA is at least one selected from me group consisting of a first siRNA, a second siRNA and a third siRNA; wherein the first siRNA is a double stranded nucleic acid comprising the sequences shown in SEQ ID NO: 9 and SEQ ID NO: 10, the second siRNA is a double stranded nucleic acid comprising the sequences shown in SEQ ID NO: 13 and SEQ ID NO: 14, and the third siRNA is a double stranded nucleic acid comprising the sequences shown in SEQ ID NO: 17 and SEQ ID NO: 18.

Other embodiments of the disclosure are methods wherein the visfatin antagonist comprises at least one compound selected from the group consisting of FK-866 and APO866.

FK-866 is a visfatin antagonist, also known as K 22.175 or N-[4-(1-benzoyl-4-piperidinyl)butyl]-3-(3-piperidinyl)-2E-propenamide, and is a highly specific, non-competitive inhibitor of visfatin which causes gradual $NAD^+$ depletion. FK~866 has a molecular formula of C24H29N3O2 and a formula weight of 391.5. FK~866 is available from Caymen Chemical, Ann Arbor, Mich., USA. The structure of FK~866 is shown below, but FK~866 molecules may also comprise derivatives of this structure.

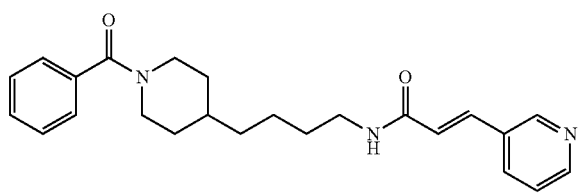 [SMILES: O=C(/C=C/c1cccnc1)NCCCCC1CCN(C(=O)c2ccccc2)CC1]

APO866 is visfatin antagonist and is as inhibitor of visfatin. APO866 is available from TopoTarget A/S, Copenhagen, Denmark. The structure of APO866 is shown below, but APO866 molecules may also comprise derivatives of these structures.

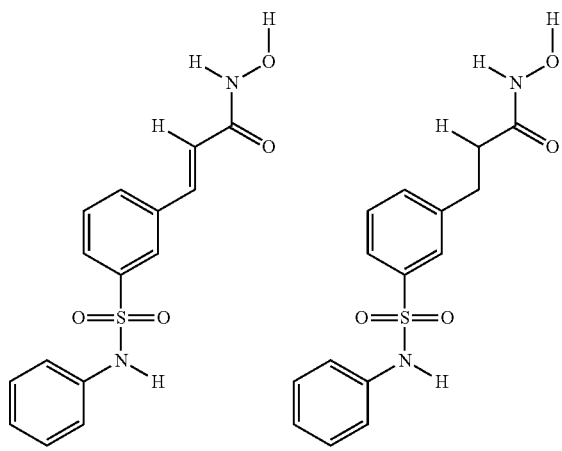 [SMILES: O=C(/C=C/c1cccc(S(=O)(=O)Nc2ccccc2)c1)NO ; O=C(CCc1cccc(S(=O)(=O)Nc2ccccc2)c1)NO]

Another aspect of the disclosure is a method of treating acne vulgaris in a subject comprising administering a therapeutically effective amount of a visfatin antagonist, or a pharmaceutical composition containing a visfatin antagonist, to a subject with acne vulgaris; whereby the acne vulgaris is treated.

Another embodiment of the disclosure is a method wherein the pharmaceutical composition containing a visfatin antagonist is a pharmaceutical composition of the disclosure.

One aspect of the disclosure is a method of treating a sebum production deficiency condition in a subject comprising administering a therapeutically effective amount of a visfatin agonist, or a pharmaceutical composition containing a visfatin agonist, to a subject with a sebum production deficiency condition; whereby the sebum production deficiency condition is treated.

Another embodiment of the disclosure is a method wherein the sebum production deficiency condition is a xerosis condition associated with at least one selected from the group consisting of chapping, dermatitis, psoriasis, diabetes, renal failure, renal transplantation, hemodialysis, vitamin A deficiency and angular cheilitis.

Other embodiments of the disclosure are methods wherein the visfatin agonist comprises at least one amino acid sequence selected from the group consisting of SEQ ID NO: 2, SEQ ID NO: 4, SEQ ID NO: 6 and SEQ ID NO: 8.

Other embodiments of the disclosure are methods wherein the visfatin agonist comprises the amino acid sequence shown in SEQ ID NO: 2.

Other embodiments of the disclosure are methods wherein the pharmaceutical composition containing a visfatin agonist is a pharmaceutical composition of the disclosure.

Another aspect of the disclosure is a method of increasing the sebum production of a subject comprising administering a therapeutically effective amount of a visfatin agonist, or a pharmaceutical composition containing a visfatin agonist, to the skin of a subject; whereby the sebum production of the subject is increased. Whether sebum production has been increased can readily be determined by measuring a first amount of sebum present on an area of skin prior to visfatin agonist administration to the area, measuring a second amount of sebum present on the area of skin after administration of a visfatin agonist to the area and confirming the second amount of sebum is larger than the first amount of sebum. Those of ordinary skill in the art will also recognize other methods for confirming sebum production has been decreased.

Another embodiment of the disclosure is a method wherein the visfatin agonist is administered topically or intradermally.

Topical administration to the skin occurs when a composition delivered to the dermis layer of the skin. Topical administration typically is performed by applying a composition to the surface of the skin.

Intradermal administration occurs when a composition is delivered below the surface of the skin to a skin layer such as the epidermis. Intradermal administration can be performed by, for example, the injection of a composition below the surface of the skin or the electroelution of a composition below the surface of the skin.

Another aspect of the disclosure is a method of decreasing the sebum production of a subject comprising administering a therapeutically effective amount of a visfatin antagonist, or a pharmaceutical composition containing a visfatin antagonist, to the skin of the subject, whereby the sebum production of the subject is decreased.

Whether sebum production has been decreased can readily be determined by measuring a first amount of sebum present on an area of skin prior to visfatin antagonist administration to the area, measuring a second amount of sebum present on the area of skin after administration of a visfatin antagonist to the area and confirming the second amount of sebum is smaller than the first amount of sebum. Those of ordinary skill in the art will also recognize other methods for confirming sebum production has been decreased.

Another embodiment of the disclosure is a method wherein the visfatin antagonist is administered topically or intradermally.

Another embodiment of the disclosure is a method wherein the pharmaceutical composition containing a visfatin antagonist is a pharmaceutical composition of the disclosure.

Another aspect of the disclosure is the use of an siRNA comprising a nucleic acid sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 9, SEQ ID NO: 10, SEQ ID NO: 13, SEQ ID NO: 14, SEQ ID NO: 17, and SEQ ID NO: 18 in the manufacture of a medicament for the treatment of a sebum-overproduction condition.

Another aspect of the disclosure is the use of an siRNA comprising a nucleic acid sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 9, SEQ ID NO: 10, SEQ ID NO: 13, SEQ ID NO: 14, SEQ ID NO: 17, and SEQ ID NO: 18 in the manufacture of a medicament for the treatment of a condition selected from the group consisting of acne, seborrhea, seborrhoeic dermatitis, a sebaceous cyst and sebaceous hyperplasia.

Another aspect of the disclosure is the use of FK-866 in the manufacture of a medicament for the treatment of a sebum-overproduction condition.

Another aspect of the disclosure is the use of FK-866 in the manufacture of a medicament for the treatment of a condition selected from the group consisting of acne, seborrhea, seborrhoeic dermatitis, a sebaceous cyst and sebaceous hyperplasia.

Another aspect of the disclosure is the use of APO866 in the manufacture of a medicament for the treatment of a sebum-overproduction condition.

Another aspect of the disclosure is the use of APO866 in the manufacture of a medicament for the treatment of a condition selected from the group consisting of acne, seborrhea, seborrhoeic dermatitis, a sebaceous cyst and sebaceous hyperplasia.

Another aspect of the disclosure is the use of an siRNA comprising a nucleic acid sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 9, SEQ ID NO: 10, SEQ ID NO: 13, SEQ ID NO: 14, SEQ ID NO: 17, and SEQ ID NO: 18 in the manufacture of a medicament for the treatment of acne vulgaris.

Another aspect of the disclosure is the use of a visfatin agonist comprising at least one amino acid sequence selected from the group consisting of SEQ ID NO: 2, SEQ ID NO: 4, SEQ ID NO: 6 and SEQ ID NO: 8 in the manufacture of a medicament for the treatment of a sebum production deficiency condition.

Another aspect of the disclosure is the use of a visfatin agonist comprising at least one amino acid sequence selected from the group consisting of SEQ ID NO: 2, SEQ ID NO: 4, SEQ ID NO: 6 and SEQ ID NO: 8 in the manufacture of a medicament for the treatment of a xerosis condition associated with at least one selected from the group consisting of chapping, dermatitis, psoriasis, diabetes, renal failure, renal transplantation, hemodialysis, vitamin A deficiency and angular cheilitis.

Another aspect of the disclosure is a pharmaceutical composition adapted for treating a sebum over-production condition in a subject comprising administering a therapeutically effective amount of a visfatin antagonist composition to a subject with a sebum over-production condition; whereby the sebum over-production condition is treated.

Another aspect of the disclosure is a pharmaceutical composition adapted for treating acne vulgaris in a subject comprising administering a therapeutically effective amount of a visfatin antagonist composition to a subject with acne vulgaris; whereby the acne vulgaris is treated.

Another aspect of the disclosure is a pharmaceutical composition adapted for treating a sebum production deficiency condition in a subject comprising administering a therapeutically effective amount of a visfatin agonist composition to a subject with a sebum production deficiency condition; whereby the sebum production deficiency condition is treated.

Another aspect of the disclosure is a pharmaceutical composition adapted for increasing the sebum production of a subject comprising administering a therapeutically effective amount of a visfatin agonist composition to the skin of a subject; whereby the sebum production of the subject is increased.

Another aspect of the disclosure is a pharmaceutical composition adapted tor decreasing the sebum production of a subject comprising administering a therapeutically effective amount of a visfatin antagonist composition to the skin of the subject, whereby the sebum production of the subject is decreased.

The present invention will now be described with reference to the following specific, non-limiting Examples.

EXAMPLES

Experimental Methods

Preparation of Paraffin Embedded Skin Sections: Skin biopsies were performed on study mice. Skin biopsy samples were fixed in 4% paraformaldehyde then dehydrated with increasing concentrations of ethanol (50-100%). Dehydrated biopsy samples were immersed twice in xylene, then once in a 1:1 solution of paraffin and xylene and finally three times in pure melted paraffin at a temperature of 60° C. Paraffin blocks were then sectioned with a microtome and the resulting sections were mounted on slides.

Preparation of Frozen Skin Sections: Skin biopsies were embedded in optimum cutting temperature compound (OCT) and immediately sectioned by cryostat-microtome and mounted on slides.

Hematoxylin & Eosin Staining: Paraffin embedded skin biopsy section slides were incubated at 60° C. for 60 minutes and deparaffinized by washing the slides twice with toluene (100%) for 10 minutes and rehydrating the skin biopsy section slides in decreasing concentration of ethanol (100-50%) for 5 minutes each. The slides then were stained with a ready to use solution of hematoxylin for 5 minutes, rinsed with water, stained with eosin (0.5% in double distilled water) for 1.5 minutes and washed twice by rapid immersion in 70% ethanol. Thereafter, the slides were dehydrated by washing once with 95% ethanol for 5 minutes, twice with 100% ethanol for 5 minutes and twice with xylene (100%) for 10 minutes. This was followed by the application of ENTELLAN™ (Merck KGaA, Darmstadt, Germany) and the mounting of coverslips.

Visfatin Immunohistochemistry: Paraffin embedded skin biopsy section slides were prepared as described above. Biopsy section slides were deparaffinized and rehydrated as described above. Antigen retrieval was performed by microwaving skin biopsy section slides in 10 mM citrate buffer (pH 6.0) for 2 minutes at maximal power and for an additional 10 minutes at 20% of the maximal power. Skin biopsy section slides were then cooled to room temperature for 1 hour. Next, skin biopsy slides were incubated with blocking solution (10% horse serum in DPBS$^{-/-}$) for 1 hour and then incubated overnight at 4° C. with a rabbit IgG$_1$ polyclonal antibody preparation specific for *Mus musculis* (~house mouse) visfatin (Phoenix Pharmaceutical Inc., Burlingame, Calif.) at a dilution of 1:200 in a solution of DPBS$^{-/-}$ containing 2% normal horse serum and 1% TRITON™ x-100 detergent overnight at 4° C. The next day, skin biopsy slides were washed three times in DPBS$^{-/-}$ and incubated with a goat-anti-rabbit IgG$_1$ biotin conjugate (Vector Laboratories, Inc., Burlingame, Calif., USA) as the secondary antibody for 90 minutes. A wash in DPBS$^{-/-}$ was then performed and slides were subjected to biotin-avidin enhancement by using the VECTASTATIN™ enhancement kit as directed by the manufacturer (Vector Laboratories Inc., Burlingame, Calif.) and developed utilizing DAB reaction. Counter staining was carried out with hematoxylin and eosin staining. Skin biopsy slides were dehydrated by sequential immersion in ethanol solutions of and increasing concentrations as described above followed by two washes with xylene (100%) for 10 minutes.

This was followed by the application of ENTELLAN™ (Merck KGaA, Darmstadt, Germany) and the mounting of coverslips mounted.

Oil Red O Staining: Frozen skin biopsy section slides were fixed in 1% neutral-buffered formalin for 5 minutes, washed in deionized water, and incubated in 60% isopropanol for 5 minutes. Skin biopsy section slides were stained with a fresh, filtered Oil Red O working solution which had been prepared immediately beforehand by making a 2:3 mixture of stock (0.5% Oil Red O in 99% isopropanol) and deionized water. Skin biopsy sections slides were transferred to 60% isopropanol, washed in deionized water, counterstained using hematoxylin and air dried and mounted with VECTASHIELD™ mounting medium. This was followed by the application of VECTASHIELD™ mounting medium (Vector Laboratories Inc., Burlingame, Calif.) and the mounting of coverslips.

Example 1

Visfatin is expressed in the sebaceous glands of the skin. See FIGS. 1A-1B. Visfatin expression in skin was studied using histological examination. Skin biopsy samples from BalbC mice (*Mus muscuius*) were prepared for histological examination using the materials and methods described above. Visfatin immunohistochemistry was also performed as described above.

Figure 1B:
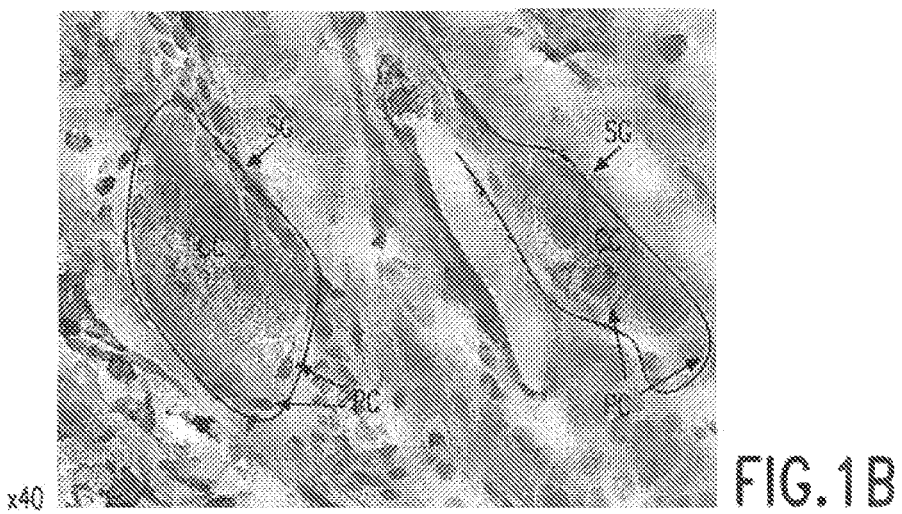

Skin biopsy samples sections were from the skin of 2 month old BalbC mice. Skin samples were fixed in 4% paraformaldehyde and paraffin embedded. Skin sections were specifically stained for visfatin (brown in FIGS. 1A-1B) using an anti-visfatin antibody as described above. In FIGS. 1A-1B "HF" means "hair follicle", "SG" means "sebaceous gland), "PC" means "peripheral cells" and "CC" means "central cells[.]" Images in FIGS. 1A-1B represent magnifications of 10× or 40× as indicated and were produced using a Nikon Eclipse 50i microscope.

As seen in FIGS. 1A-1B visfatin is predominantly, and specifically, expressed in the sebaceous glands of the skin. In particular, visfatin expression is distinctly localized to the lobular area of the sebaceous glands. See FIGS. 1A-1B. Visfatin was also expressed at low levels in the hair follicles and the dermis. See FIGS. 1A-1B. As shown in FIGS. 1A-1B, visfatin expression is restricted to the round, bubble-shaped cells present in the sebaceous glands. The morphological features of these cells are characteristic of sebocytes and the differentiated sebocyte precursor cells. Importantly, these are the cells which fill with the lipid components of sebum and rupture to secrete sebum into the interior of sebaceous glands and indicates visfatin plays an important role in sebum production.

Example 2

Visfatin is highly expressed in the sebum accumulating cells present in the interior of the sebum gland. See FIGS. 2A-2B. Skin biopsy samples from BalbC mice were prepared for histological examination using the materials and methods described above. Visfatin immunohistochemistry and Oil Red O staining was also performed as described above.

Skin biopsy samples sections were from the skin of 2 month old BalbC mice. Skin samples were fixed in 4% paraformaldehyde and paraffin embedded. Skin sections were specifically stained for visfatin (brown in FIGS. 2A-2B) using an anti-visfatin antibody as described above. Skin sections were also stained with Oil Red O to identify accumulations of lipids, such as sebum lipids. Images in FIGS. 2A-2B represent magnifications of 40× as indicated and were produced using a Nikon Eclipse 50i microscope.

Figures 2A, 2B:
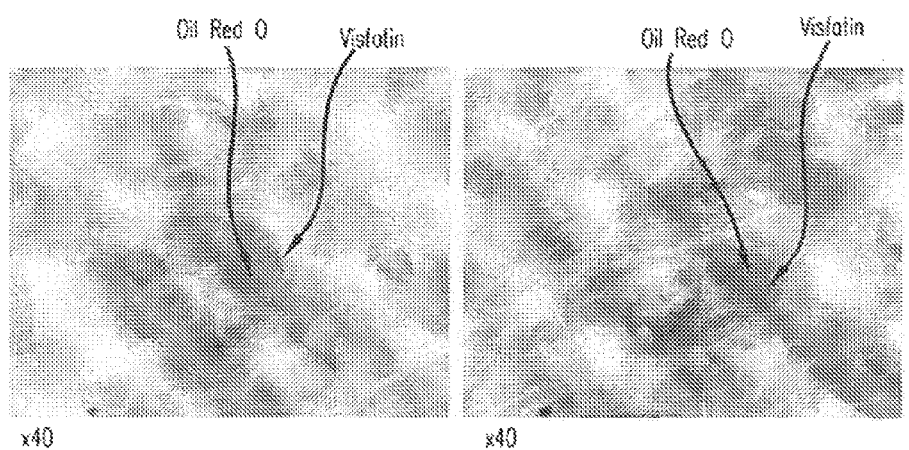
FIGS. 2A-2B show that visfatin is expressed in sebum-accumulating cells of the sebaceous glands.
Figure 3E:
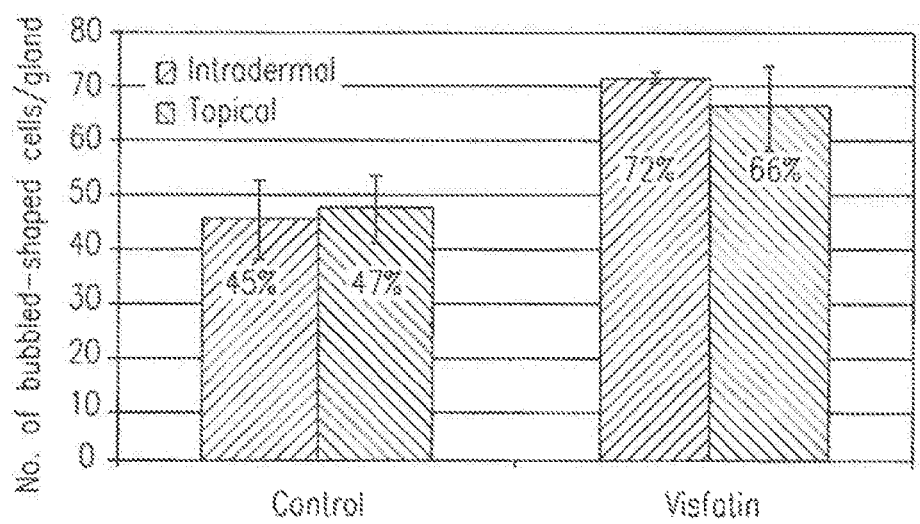

As seen in FIGS. 2A-2B visfatin expression and a large pool of lipids are clearly co-localized within those cells having morphological features characteristic of sebocytes and differentiated sebocyte prescursor cells. The results in FIGS. 2A-2B confirm visfatin is highly expressed in sebum accumulating cells and is closely associated with the production of sebum in the interior of sebaceous glands. These results also confirm these cells located in the interior of the sebaceous glands, which have a bubble shaped morphology and stain positive with Oil Red O, are lipid accumulating sebocytes.

Example 3

Topical administration and intradermal administration of visfatin increases the number of sebocytes located inside of the sebaceous glands. See FIGS. 3A-3E.

A stock preparation of recombinant. *Mus musculus* visfatin (Enzo Life Sciences Inc., Farmingdale, N.Y., USA) was prepared in 0.1 M ammonium bicarbonate buffer solution. This stock solution was then used to prepare a topical solution comprising 0.01 μg/ml of recombinant, *Mus musculus* visfatin in PBS. The stock solution was also used to prepare an intradermal solution comprising 0.01 μg/ml of recombinant, *Mus musculus* visfatin in PBS containing 0.1% (v/v) DMSO. Adult BalbC mice having an average body weight of 25 g then received either 200 μL of the topical solution by topical administration to the skin treatment area and the use of sterile gauze or 200 μL of the intradermal solution by injection into the skin treatment area. Mice were treated in this fashion with the topical solution or intradermal solution delivered once daily to the skin treatment area for 4 days. Skin biopsy samples from the treated areas of the mice were then prepared for histological examination using the materials and methods described above. Hematoxylin and eosin (H&E) staining was also performed as described above.

Skin samples were fixed in 4% paraformaldehyde and paraffin embedded. The number of cells with the bubbled shaped morphology characteristic of sebocytes were then counted and calculated as a percentage of the number of total cells in each sebaceous gland by microscopic examination at a magnification of 40× using a Nikon Eclipse 50i microscope.

As seen in FIGS. 3A-3E, both the intradermal administration and topical administration of visfatin increased the number of sebocytes present inside the sebaceous glands of treated mice relative to control mice. Similar results were also obtained in otherwise identically conducted studies by treatment with topical solutions and intradermal solutions containing 0.001 μg/ml of recombinant, *Mus musculus* visfatin. Importantly, these results demonstrate that intradermal or topical treatment with compositions comprising visfatin induce the accumulation of sebocyte cells inside sebaceous glands. These results also indicate that visfatin treatment of the skin can induce symptoms, such as the formation of sebaceous plugs, associated with acne.

Example 4

Visfatin treatment increases lipid accumulation in sebaceous glands relative to controls. Sec FIGS. 4A-4D. Visfatin treatment also induces the maturation of sebaceous glands in the skin, and the production of sebum by these matured sebaceous glands, relative to controls. See FIGS. 4A-4D.

Newborn BalbC mice (*Mus musculus*) having an average body weight of 2 g after birth, then received either 100 μL of the topical solution described in Example 3 above by topical administration to the skin treatment area and the use of sterile gauze or 100 μL of the intradermal solution described in Example 3 above by injection into the skin treatment area. Newborn mice were treated in this fashion with 100 μL of the topical solution or intradermal solution delivered once daily to the skin treatment area for 4 days.

Skin biopsy samples from the treated areas of the newborn mice were then prepared on day 3, and day 4, after birth for histological examination using the materials and methods described above. Hematoxylin and eosin (H&E) staining and Oil Red O was also performed as described above. Skin biopsy samples in FIGS. 4A-4B were prepared on day 3 after birth. Skin biopsy samples in FIGS. 4A-4B are stained with hematoxylin and Oil Red O. Black arrows in FIG. 4B identify sebum containing sebaceous glands. Skin biopsy samples in FIGS. 4C-4D are stained with hematoxylin and eosin. Red arrows in FIG. 4D identify sebaceous glands. Skin samples were fixed in 4% paraformaldehyde and paraffin embedded.

Newborn mice are known not to secrete sebum during the first few days after their birth. However, several days after birth the sebaceous glands eventually mature and start to secrete sebum.

As seen in FIG. 4A, at day 3 after birth the sebaceous glands of newborn mice topically treated with control solution do not contain sebum based on Oil Red O staining. Thus, at day 3 after birth the sebaceous glands in these newborn, control mice are immature and unable to produce sebum.

In stark contrast, FIG. 4B shows that at day 3 after birth the sebaceous glands of newborn mice topically treated with visfatin do contain sebum based on Oil Red O staining. Thus, visfatin can induce maturation of the sebum glands and increased sebum production relative to control mice at day 3 after birth.

FIG. 4C confirms these results and shows, based on H&E staining, that at day 4 after birth the most of the sebaceous glands of newborn mice topically treated with control solution lacked the characteristics of mature sebaceous glands and did not contain flattened cells at the gland periphery or bubble-shaped, sebocyte cells in the interior of the gland.

FIG. 4D also shows, based on H&E staining, that at day 4 after birth the sebaceous glands newborn mice topically treated with control solution had the characteristics of mature sebaceous glands and contain flattened cells at the gland periphery and bubble-shaped, sebocyte cells in the interior of the mature gland.

Importantly, these results demonstrate visfatin treatment induces the maturation of sebaceous glands and increases sebum production. Most importantly, these results indicate that increasing visfatin activity can increase sebum production in conditions related to sebum production Example 5

Treatment with a visfatin antagonist inhibits sebum production in sebaceous glands. See FIGS. 5A-5F and FIG. 6.

Two small interfering nucleic acids (siRNAs) designated siRNA1 and siRNA2 targeting RNA transcripts corresponding to the *Mus musculus* visfatin encoding cDNA sequence shown in SEQ ID NO: 3 were prepared. siRNA1 was a double-stranded nucleic acid comprising a hybridized duplex of the sequence 5'-gcacaguaccauaacggcutt-3' (SEQ ID NO: 11) and the sequence 5'-agccguuauggguacugugctt-3' (SEQ ID NO: 12). siRNA2 was a double-stranded nucleic acid comprising a hybridized duplex of the sequence 5'-ggucuuagauauuuuaggctt-3' (SEQ ID NO: 15) and the sequence 5'-gc-cuaaaauaucuaagaccctt-3' (SEQ ID NO: 16). These siRNAs were purchased from Applied Biosystems Inc. (Ambion), Austin, Tex., US.

Topical solutions containing both siRNA1 and siRNA2 were then prepared. The final concentration of all siRNAs combined in each topical solution was either 1 nM or 3 nM. Importantly, siRNA1 and siRNA2 were both present in each topical solution at equimolar amounts to produce the final 1 nM or 3 nM combined siRNA concentration.

Two types of topical solutions for siRNA delivery were prepared. The first solution comprised siRNA1 and siRNA2 in PBS containing 0.1% (v/v) DMSO. This first solution was used to administer the "naked siRNA" in FIG. 6A. The second solution comprised siRNA 1 and siRNA2 in PBS containing 0.1% (v/v) DMSO and 1 μg/ml of a cationic, lipophilic, N-myristoylated peptide having the amino acid sequence FARKGALRQ (SEQ ID NO: 27). This cationic, lipophilic, N-myristoylated peptide was named "MPDY" and prepared by covalently attaching myristoylic acid to the alpha-amino group of the amino terminal F residue of SEQ ID NO: 27 via an amide bond formed by a N-myristoyl-transferase catalyzed reaction. This second solution was used to administer the "siRNA delivered by a delivery system" in FIG. 6B and to produce the results shown in FIGS. 5A-5F.

Figure 6A:
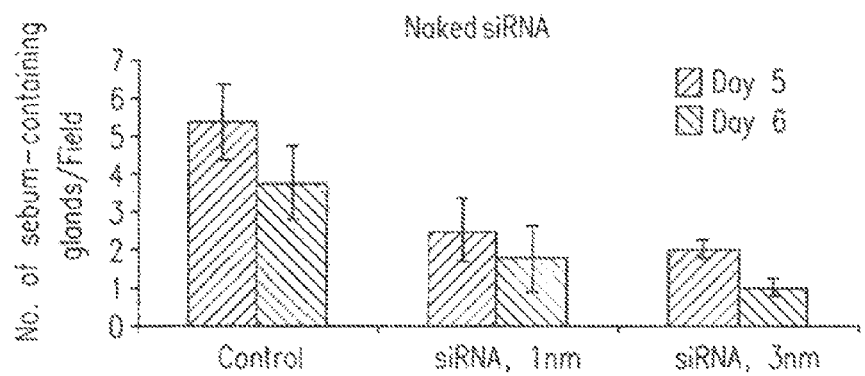
FIGS. 6A-6B show that topical treatment with a visfatin antagonist siRNA suppresses sebum production in the sebaceous glands.
Figure 6B:
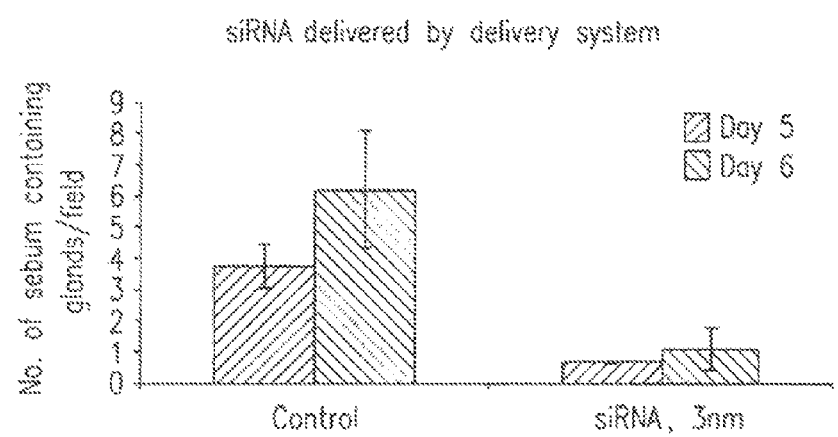

Newborn BalbC mice were treated with the second solution containing the siRNAs at 1 nM (FIG. 6B) or 3 nM (FIGS. 5A-5F and FIG. 6B). Newborn BalbC mice (*Mus musculus*) were also treated with the first solution containing the siRNAs at 1 nM (FIG. 6A) or 3 nM (FIG. 6B). At days 1 to 3 after birth the average body weight of the newborn BalbC mice was 2 g and 100 μL of either the first solution or second solution was applied once daily by the use of sterile gauze to a treatment area on the skin of the mice. At days 4 to 6 after birth the average body weight of the newborn BalbC mice was 3 g and 200 μL of either the first solution or second solution the siRNA topical solution was applied once daily by the use of sterile gauze to a treatment area on the skin of the mice. Newborn mice were also treated topically with either a siRNA free first control solution containing the first solution (FIGS. 6A-6B) or a siRNA free second control solution containing the second solution (FIG. 5 and FIGS. 6A-6B) once daily to the skin treatment area for the first 6 days after birth. Skin biopsy samples from the treated areas of the newborn mice were then prepared on days 5, and 6, after birth for histological examination using the materials and methods described above. Visfatin immunohistochemistry was performed as described above. Hematoxylin and eosin (H&E) staining and Oil Red O was also performed as described above. Skin samples were fixed in 4% paraformaldehyde and paraffin embedded.

Skin biopsy samples in FIGS. 5A-5F were prepared on day 5. Skin biopsy samples in FIGS. 5A-5B are stained for visfatin expression. Yellow arrows in FIGS. 5A-5B identify visfatin specific staining. Skin biopsy samples in FIGS. 5C-5D are stained with hematoxylin and Oil Red O. Black arrows in FIGS. 5C-5D identify sebaceous glands. Skin biopsy samples in FIGS. 5E-5F are stained with hematoxylin and eosin. Red arrows in FIGS. 5E-5F identify mature sebaceous glands containing bubble-shaped, sebocyte cells.

The number of cells with the bubbled shaped morphology characteristic of sebocyte cells in skin biopsy samples prepared on days 5, and 6, were also counted and calculated as a percentage of the number of total cells in each sebaceous gland by microscopic examination at a magnification of 40× using a Nikon Eclipse 50i microscope. FIGS. 6A-6B.

As seen in FIG. 5A, at day 5 after birth a high level of visfatin expression was detected in the skin of newborn mice topically treated with the second control solution. Moreover, this visfatin expression appeared to be predominantly associated with the sebaceous glands.

In stark contrast, FIG. 5B shows a clear inhibition of visfatin expression in the skin and sebaceous glands of newborn mice at day 5 after birth following topical treatment with the second solution containing 3 nM of the visfatin antagonist siRNAs daily. Thus, the visfatin antagonists siRNA1 and siRNA2 can inhibit visfatin expression in skin and sebum glands.

As seen in FIG. 5C, at day 5 after birth the sebaceous glands of newborn mice topically treated with control solution contain sebum based on Oil Red O staining. Thus, at day 5 after birth the sebaceous glands in these newborn, control mice are mature and able to produce sebum. These results also indicate the MPDY peptide alone did not inhibit sebum production or otherwise discernibly alter the skin.

In contrast, FIG. 5D shows that at day 5 after birth the sebaceous glands of newborn mice topically treated with the second solution containing 3 nM of visfatin antagonist siRNAs daily do contain sebum based on Oil Red O staining. Thus, the visfatin antagonists siRNA1 and siRNA2 inhibit sebum production by the sebaceous glands and can control sebum levels.

FIG. 5E confirms these results and shows, based on H&E staining, that at day 5 alter birth the sebaceous glands of newborn mice topically treated with the second control solution had the characteristics of mature sebaceous glands and contained flattened cells at the gland periphery and bubble-shaped, sebocyte cells in the interior of the mature gland. These results again indicate the MPDY peptide alone did not inhibit sebum production or otherwise discernibly alter the skin.

FIG. 5F also shows, based on H&E staining, that at day 5 after birth the sebaceous glands newborn mice topically treated with the second solution containing 3 nM of the visfatin antagonist siRNAs daily lacked the characteristics of mature sebaceous glands and did not appear to contain bubble-shaped, sebocyte cells in the interior of the mature gland.

FIG. 6A shows that topical treatment with the first solution containing either 1 nM or 3 nM of the visfatin antagonist siRNAs daily decreased the number of sebum containing sebaceous glands in the skin of visfatin antagonist treated animals relative to control animals treated with control solution. These results also demonstrate the effects produced by the visfatin antagonist siRNAs were dose dependent.

FIG. 6B similarly shows that topical treatment with the second solution containing 3 nM of visfatin antagonist siRNAs daily decreased the number of sebum containing sebaceous glands in the skin of treated animals.

Additionally, a comparison of the results in FIG. 6A and FIG. 6B indicate a more prominent inhibition in the number of sebum containing sebaceous glands in the skin occurred when the visfatin antagonist siRNAs were topically administered in the second solution of PBS containing 0.1% (v/v) DMSO and 1 µg/ml of the cationic, lipophilic MPDY peptide relative to the first solution lacking this peptide. Together these results indicate a more efficient delivery of visfatin antagonist siRNAs occurs in solutions containing this cationic, lipophilic peptide.

These results demonstrate that visfatin antagonists, such as siRNAs, can inhibit the expression of visfatin and decrease, or control, sebum production by the sebaceous glands in the skin. These results also indicate that visfatin activity is necessary for sebum production by the sebaceous glands.

Most importantly, these results demonstrate visfatin antagonist treatment can be used to control sebum production and treat acne as well as other conditions, such as seborrhea, associated with increased sebum production.

Example 6

Compositions comprising visfatin effectively treat moderately, to severely, dry skin. See Table 1.

Women ranging in age from their twenties to older and having moderately, to severely, dry skin were identified and became patient volunteers. A cream formulation designated "Test Product A" and containing 1% (w/w) (0.1 µg/ml) recombinant human visfatin, 95% water, 0.2% (w/w) montan wax, 0.2% (w/w) bee wax, 0.2% (w/w) sorbitol, 0.2% (w/w) shea butter, 1% (w/w) borage oil, 1% (w/w) calendula oil, 0.2% (w/w) Hamamelis extract and 1% (w/w) castor oil was prepared.

Patient volunteers participating in the study washed a moderately, to severely dry, area of their skin with a mild soap, rinsed the area clean and topically applied test product A to this area of their skin. This was done twice daily (approximately once every twelve hours) during the study period. The study period was three months. At the conclusion of the three month study period the patient volunteers completed a questionnaire containing the statements in Table 1.

TABLE 1

| Item | Statement | % of patient volunteers that agree with the statement |
| --- | --- | --- |
| 1 | I have moderate to serve dry skin | 100% |
| 2 | My condition is uncomfortable and negatively affects my well being. | 100% |
| 3 | I have previously used various products that contained urea and lactic acid. | 100% |
| 4 | My skin problem persisted despite the use of moisturizing products. | 100% |
| 5 | The test product A was easy to apply. | 100% |
| 6 | The test product A texture and smell was pleasant. | 80% |
| 7 | Following application of test product A, my skin became softer. | 100% |
| 8 | Following application of test product A, my skin became less scaly and itchy. | 100% |
| 9 | Following application of test product A, my skin became more oily. | 80% |
| 10 | Following application of test product A, my skin became more shiny and bright. | 100% |
| 11 | Generally the test product A tested my dry skin problem effectively. | 100% |
| 12 | My well being was improved following the use of test product A. | 100% |
| 13 | I will use the test product A if my dry skin problem perists. | 100% |

The percentage of patients agreeing with each statement in Table 1 is indicated. As shown in Table 1 all patient volunteers had moderately, to severely, dry skin which was uncomfortable and negatively affected their well being. Table 1 also shows that all patient volunteers agreed their skin became softer, less scaly and itchy as well as more shiny and bright. Most importantly, all patient volunteers agreed the topical application of the composition comprising visfatin treated their dry skin problem effectively and that their well being was improved following the use of the composition. See Table 1. These improvements in patient volunteers' dry skin conditions were typically seen at day 5, or day 6, of participation in the study, but was also seen even earlier for some patient volunteers (such as younger women in their twenties).

The present disclosure now being fully described, it will be apparent to one of ordinary skill in the art that many changes and modifications can be made thereto without departing from the spirit or scope of the appended claims.

DETAILED DESCRIPTION OF THE FIGURES

FIGS. 1A-1B

FIGS. 1A-1B show visfatin expression is restricted to the sebaceous glands.

Histological sections of skin from 2 month old BalbC mice were prepared. Skin samples were fixed in 4% paraformaldehyde and paraffin embedded. Skin sections were stained for visfatin (brown) with an anti visfatin antibody. HF (hair follicle), SG (sebaceous gland), PC (peripheral cells), CC (central cells). Magnification ×10 and ×40. Microscope: Nikon Eclipse 50i.

FIGS. 2A-2B

FIGS. 2A-2B show visfatin is expressed in sebum-accumulating cells of the sebaceous gland. Frozen sections were prepared from skin of 2 months old BalC mice as described in Material and Methods, fixed in 4% paraformaldehyde and subjected to visfatin (brown) and Oil Red O (red) staining. Magnification ×10 and ×40. Microscope: Nikon Eclipse 50i.

FIGS. 3A-3E

FIGS. 3A-3E show visfatin increases the number of bubbled-shaped, sebocyte cells in sebaceous glands.

Adult BalbC mice were treated intradermaly or topically with visfatin (0.01 µg/ml) for 4 days. After 4 days, skin sections of treated areas were collected, fixed in 4% paraformaldehyde, paraffin embedded and skin sections were H&E stained. Magnification: ×40. Microscope: Nikon Eclipse 501. FIGS. 3A-3D show micrographs of the skin biopsy samples. FIG. 3F shows data obtained by counting bubbled-shaped, sebocyte cells located in the center of the sebaceous glands and calculating the percentage of such sebocyte cells relative to the total cells present in the sebaceous glands for each one of the treatments.

FIGS. 4A-4D

FIGS. 4A-4D show topical treatment with visfatin induces maturation and lipid accumulation in the sebaceous glands.

Newborn BalbC mice were treated topically with visfatin for 3 days. Skin biopsies were taken at the indicated time points. In FIGS. 4A-4B, frozen skin sections were prepared, stained with Oil Red O and counterstained with hematoxylin. Black arrows indicate sebum-containing glands. In FIGS. 4C-4D paraffin sections were prepared and subjected to H&E staining. Red arrows indicate sebaceous glands. Magnification ×20. Microscope: Nikon Eclipse 50i.

FIGS. 5A-5F

FIGS. 5A-5F show that topical treatment with visfatin antagonist siRNAs suppresses sebum production in the sebaceous glands.

Newborn BalbC mice were treated topically with both visfatin antagonist siRNA1 and siRNA2 at a 3 nM combined siRNA concentration with the cationic, lipophilic MPDY peptide for 5 days. Skin biopsies were taken at the indicated time points. Paraffin sections were prepared and, in FIGS. 5A-5B, immunostained for visfatin in order to demonstrate visfatin inhibition. Yellow arrows indicate visfatin staining. In FIGS. 5C-5D, frozen skin sections were prepared, stained with Oil Red O and counterstained with hematoxylin. Black arrows indicate sebum-containing glands. In FIG. 5C, H&E staining of biopsy samples was performed. Red arrows indicate mature sebaceous glands.

FIGS. 6A-6B

FIGS. 6A-6B show topical treatment with visfatin antagonist siRNAs suppresses sebum production in the sebaceous glands.

Newborn BalbC mice were treated topically with visfatin antagonist siRNA1 and siRNA2 at a 1 nM, or 3 nM, combined siRNA concentration with the cationic, lipophilic MPDY peptide (FIG. 6B), or without this peptide (FIG. 6A) for 5 days. Skin biopsies were taken at the indicated time points. Frozen sections were prepared and stained for Oil Red O as described in Materials & Methods. Sebum containing glands were counted and the results are summarized in the graphs of FIGS. 6A-6B.

The invention claimed is:

1. A method of treating a sebum over-production condition in a subject in need wherein said method comprises topically administering a therapeutic amount of a visfatin antagonist to the subject in need; wherein said visfatin antagonist comprises:
   a) FK-866;
   b) at least one siRNA comprising a nucleic acid sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 9, SEQ ID NO:10, SEQ ID NO: 13, SEQ ID NO: 14, SEQ ID NO: 17, and SEQ ID NO: 18; or
   c) both (a) and (b)

wherein the sebum over-production condition is selected from the group consisting of acne, seborrhea, seborrhoeic dermatitis, a sebaceous cyst and sebaceous hyperplasia.

2. The method according to claim 1, wherein the sebum over-production condition is acne.

3. The method according to claim 2, wherein the acne is acne vulgaris.

4. The method according to claim 1 further comprising administering an amino terminally myristoylated delivery peptide having the amino acid sequence shown in SEQ ID NO: 27.

* * * * *

SEQUENCE LISTING

```
<160> NUMBER OF SEQ ID NOS: 28

<210> SEQ ID NO 1
<211> LENGTH: 1395
<212> TYPE: DNA
<213> ORGANISM: Homo sapiens

<400> SEQUENCE: 1
ccacccaaca caagcaaagt ttattcctac tttgaatgcc gtgaaaagaa gacagaaaac      60
tccaaattaa ggaaggtgaa atatgaggaa acagtatttt atgggttgca gtacattctt     120
aataagtact taaaaggtaa agtagtaacc aaagagaaaa tccaggaagc caaagatgtc     180
tacaaagaac atttccaaga tgatgtcttt aatgaaaagg gatggaacta cattcttgag     240
aagtatgatg ggcatcttcc aatagaaata aaagctgttc ctgagggctt tgtcattccc     300
agaggaaatg ttctcttcac ggtggaaaac acagatccag agtgttactg gcttacaaat     360
tggattgaga ctattcttgt tcagtcctgg tatccaatca cagtggccac aaattctaga     420
gagcagaaga aaatattggc caaatatttg ttagaaactt ctggtaactt agatggtctg     480
gaatacaagt tacatgattt tggctacaga ggagtctctt cccaagagac tgctggcata     540
ggagcatctg ctcacttggt taacttcaaa ggaacagata cagtagcagg acttgctcta     600
```

```
attaaaaaat attatggaac gaaagatcct gttccaggct attctgttcc agcagcagaa      660
cacagtacca taacagcttg ggggaaagac catgaaaaag atgcttttga acatattgta      720
acacagtttt catcagtgcc tgtatctgtg gtcagcgata gctatgacat ttataatgcg      780
tgtgagaaaa tatggggtga agatctaaga catttaatag tatcaagaag tacacaggca      840
ccactaataa tcagacctga ttctggaaac cctcttgaca ctgtgttaaa ggttttggag      900
attttaggta agaagtttcc tgttactgag aactcaaagg gttacaagtt gctgccacct      960
tatcttagag ttattcaagg ggatggagta gatattaata ccttacaaga gattgtagaa     1020
ggcatgaaac aaaaaatgtg gagtattgaa aatattgcct tcggttctgg tggaggtttg     1080
ctacagaagt tgacaagaga tctcttgaat tgttccttca agtgtagcta tgttgtaact     1140
aatggccttg ggattaacgt cttcaaggac ccagttgctg atcccaacaa aaggtccaaa     1200
aagggccgat tatctttaca taggacgcca gcagggaatt ttgttacact ggaggaagga     1260
aaaggagacc ttgaggaata tggtcaggat cttctccata ctgtcttcaa gaatggcaag     1320
gtgacaaaaa gctattcatt tgatgaaata agaaaaaatg cacagctgaa tattgaactg     1380
gaagcagcac atcat                                                     1395

<210> SEQ ID NO 2
<211> LENGTH: 465
<212> TYPE: PRT
<213> ORGANISM: Homo sapiens

<400> SEQUENCE: 2

Pro Pro Asn Thr Ser Lys Val Tyr Ser Tyr Phe Glu Cys Arg Glu Lys
1               5                   10                  15

Lys Thr Glu Asn Ser Lys Leu Arg Lys Val Lys Tyr Glu Glu Thr Val
            20                  25                  30

Phe Tyr Gly Leu Gln Tyr Ile Leu Asn Lys Tyr Leu Lys Gly Lys Val
        35                  40                  45

Val Thr Lys Glu Lys Ile Gln Glu Ala Lys Asp Val Tyr Lys Glu His
    50                  55                  60

Phe Gln Asp Asp Val Phe Asn Glu Lys Gly Trp Asn Tyr Ile Leu Glu
65                  70                  75                  80

Lys Tyr Asp Gly His Leu Pro Ile Glu Ile Lys Ala Val Pro Glu Gly
                85                  90                  95

Phe Val Ile Pro Arg Gly Asn Val Leu Phe Thr Val Glu Asn Thr Asp
            100                 105                 110

Pro Glu Cys Tyr Trp Leu Thr Asn Trp Ile Glu Thr Ile Leu Val Gln
        115                 120                 125

Ser Trp Tyr Pro Ile Thr Val Ala Thr Asn Ser Arg Glu Gln Lys Lys
    130                 135                 140

Ile Leu Ala Lys Tyr Leu Leu Glu Thr Ser Gly Asn Leu Asp Gly Leu
145                 150                 155                 160

Glu Tyr Lys Leu His Asp Phe Gly Tyr Arg Gly Val Ser Ser Gln Glu
                165                 170                 175

Thr Ala Gly Ile Gly Ala Ser Ala His Leu Val Asn Phe Lys Gly Thr
            180                 185                 190

Asp Thr Val Ala Gly Leu Ala Leu Ile Lys Lys Tyr Tyr Gly Thr Lys
        195                 200                 205

Asp Pro Val Pro Gly Tyr Ser Val Pro Ala Ala Glu His Ser Thr Ile
    210                 215                 220
```

```
Thr Ala Trp Gly Lys Asp His Glu Lys Asp Ala Phe Glu His Ile Val
225                 230                 235                 240

Thr Gln Phe Ser Ser Val Pro Val Ser Val Ser Asp Ser Tyr Asp
            245                 250                 255

Ile Tyr Asn Ala Cys Glu Lys Ile Trp Gly Glu Asp Leu Arg His Leu
            260                 265                 270

Ile Val Ser Arg Ser Thr Gln Ala Pro Leu Ile Ile Arg Pro Asp Ser
            275                 280                 285

Gly Asn Pro Leu Asp Thr Val Leu Lys Val Leu Glu Ile Leu Gly Lys
            290                 295                 300

Lys Phe Pro Val Thr Glu Asn Ser Lys Gly Tyr Lys Leu Leu Pro Pro
305                 310                 315                 320

Tyr Leu Arg Val Ile Gln Gly Asp Gly Val Asp Ile Asn Thr Leu Gln
            325                 330                 335

Glu Ile Val Glu Gly Met Lys Gln Lys Met Trp Ser Ile Glu Asn Ile
            340                 345                 350

Ala Phe Gly Ser Gly Gly Leu Leu Gln Lys Leu Thr Arg Asp Leu
            355                 360                 365

Leu Asn Cys Ser Phe Lys Cys Ser Tyr Val Val Thr Asn Gly Leu Gly
370                 375                 380

Ile Asn Val Phe Lys Asp Pro Val Ala Asp Pro Asn Lys Arg Ser Lys
385                 390                 395                 400

Lys Gly Arg Leu Ser Leu His Arg Thr Pro Ala Gly Asn Phe Val Thr
            405                 410                 415

Leu Glu Glu Gly Lys Gly Asp Leu Glu Glu Tyr Gly Gln Asp Leu Leu
            420                 425                 430

His Thr Val Phe Lys Asn Gly Lys Val Thr Lys Ser Tyr Ser Phe Asp
            435                 440                 445

Glu Ile Arg Lys Asn Ala Gln Leu Asn Ile Glu Leu Glu Ala Ala His
            450                 455                 460

His
465

<210> SEQ ID NO 3
<211> LENGTH: 1395
<212> TYPE: DNA
<213> ORGANISM: Mus musculus

<400> SEQUENCE: 3
ccacccaaca caagcaaagt ttattcctac tttgaatgcc gtgaaaagaa gacagaaaac      60
tccaaagtaa ggaaggtgaa atacgaggaa acagtatttt atgggttgca gtacattctt     120
aataagtact aaaaggtaa agtagtgacc aaagagaaaa tccaggaggc caaagaagtg     180
tacagagaac atttccaaga tgatgtcttt aacgaaagag gatggaacta catccttgag     240
aaatacgatg gtcatctccc gattgaagta aaggctgttc ccgagggctc tgtcatcccc     300
agagggaacg tgctgttcac agtggaaaac acagacccag agtgctactg gcttaccaat     360
tggattgaga ctattcttgt tcagtcctgg tatccaatta cagtggccac aaattccaga     420
gaacagaaga aaatactggc caaatatttg ttagaaaccct ctggtaactt agatggtctg     480
gaatacaagt tacatgactt tggttacaga ggagtctctt cgcaagagac tgctggcata     540
ggggcatctg ctcatttggt taactttaaa ggaacagata ctgtggcggg aattgctcta     600
attaaaaaat actatgggac aaaagatcct gttccaggct attctgttcc agcagcagag     660
cacagtacca aacggcttg ggggaaagac catgagaaag atgcttttga acacatagta     720
```

```
acacagttct catcagtgcc tgtgtctgtg gtcagcgata gctatgacat ttataatgcg      780
tgtgagaaaa tatggggtga agacctgaga catctgatag tatcgagaag tacagaggca      840
ccactaatca tcagacctga ctctggaaat cctcttgaca ctgtattgaa ggtcttagat      900
attttaggca agaagtttcc tgttactgag aactcaaaag ctacaagtt gctgccacct       960
tatcttagag tcattcaagg agatggcgtg gatatcaata ctttacaaga gattgtagag     1020
ggaatgaaac aaaagaagtg gagtatcgag aatgtctcct tcggttctgg tggcgctttg     1080
ctacagaagt taacccgaga cctcttgaat tgctccttca agtgcagcta tgttgtaacc     1140
aatggccttg gggttaatgt gtttaaggac ccagttgctg atcccaacaa aggtcaaaa      1200
aagggccggt tatctttaca taggacacca gcggggaact tgttacact tgaagaagga      1260
aaaggagacc ttgaggaata tggccatgat cttctccata cggttttcaa gaatgggaag     1320
gtgacaaaaa gctactcatt tgatgaagtc agaaaaaatg cacagctgaa catcgagcag     1380
gacgtggcac ctcat                                                     1395

<210> SEQ ID NO 4
<211> LENGTH: 465
<212> TYPE: PRT
<213> ORGANISM: Mus musculus

<400> SEQUENCE: 4

Pro Pro Asn Thr Ser Lys Val Tyr Ser Tyr Phe Glu Cys Arg Glu Lys
1               5                   10                  15

Lys Thr Glu Asn Ser Lys Val Arg Lys Val Lys Tyr Glu Glu Thr Val
            20                  25                  30

Phe Tyr Gly Leu Gln Tyr Ile Leu Asn Lys Tyr Leu Lys Gly Lys Val
        35                  40                  45

Val Thr Lys Glu Lys Ile Gln Glu Ala Lys Glu Val Tyr Arg Glu His
    50                  55                  60

Phe Gln Asp Asp Val Phe Asn Glu Arg Gly Trp Asn Tyr Ile Leu Glu
65                  70                  75                  80

Lys Tyr Asp Gly His Leu Pro Ile Glu Val Lys Ala Val Pro Glu Gly
                85                  90                  95

Ser Val Ile Pro Arg Gly Asn Val Leu Phe Thr Val Glu Asn Thr Asp
            100                 105                 110

Pro Glu Cys Tyr Trp Leu Thr Asn Trp Ile Glu Thr Ile Leu Val Gln
        115                 120                 125

Ser Trp Tyr Pro Ile Thr Val Ala Thr Asn Ser Arg Glu Gln Lys Lys
    130                 135                 140

Ile Leu Ala Lys Tyr Leu Leu Glu Thr Ser Gly Asn Leu Asp Gly Leu
145                 150                 155                 160

Glu Tyr Lys Leu His Asp Phe Gly Tyr Arg Gly Val Ser Ser Gln Glu
                165                 170                 175

Thr Ala Gly Ile Gly Ala Ser Ala His Leu Val Asn Phe Lys Gly Thr
            180                 185                 190

Asp Thr Val Ala Gly Ile Ala Leu Ile Lys Lys Tyr Tyr Gly Thr Lys
        195                 200                 205

Asp Pro Val Pro Gly Tyr Ser Val Pro Ala Ala Glu His Ser Thr Ile
    210                 215                 220

Thr Ala Trp Gly Lys Asp His Glu Lys Asp Ala Phe Glu His Ile Val
225                 230                 235                 240

Thr Gln Phe Ser Ser Val Pro Val Ser Val Val Ser Asp Ser Tyr Asp
```

```
                   245                 250                 255
Ile Tyr Asn Ala Cys Glu Lys Ile Trp Gly Glu Asp Leu Arg His Leu
            260                 265                 270
Ile Val Ser Arg Ser Thr Glu Ala Pro Leu Ile Ile Arg Pro Asp Ser
        275                 280                 285
Gly Asn Pro Leu Asp Thr Val Leu Lys Val Leu Asp Ile Leu Gly Lys
    290                 295                 300
Lys Phe Pro Val Thr Glu Asn Ser Lys Gly Tyr Lys Leu Leu Pro Pro
305                 310                 315                 320
Tyr Leu Arg Val Ile Gln Gly Asp Gly Val Asp Ile Asn Thr Leu Gln
                325                 330                 335
Glu Ile Val Glu Gly Met Lys Gln Lys Lys Trp Ser Ile Glu Asn Val
            340                 345                 350
Ser Phe Gly Ser Gly Ala Leu Leu Gln Lys Leu Thr Arg Asp Leu
        355                 360                 365
Leu Asn Cys Ser Phe Lys Cys Ser Tyr Val Val Thr Asn Gly Leu Gly
    370                 375                 380
Val Asn Val Phe Lys Asp Pro Val Ala Asp Pro Asn Lys Arg Ser Lys
385                 390                 395                 400
Lys Gly Arg Leu Ser Leu His Arg Thr Pro Ala Gly Asn Phe Val Thr
                405                 410                 415
Leu Glu Glu Gly Lys Gly Asp Leu Glu Glu Tyr Gly His Asp Leu Leu
            420                 425                 430
His Thr Val Phe Lys Asn Gly Lys Val Thr Lys Ser Tyr Ser Phe Asp
        435                 440                 445
Glu Val Arg Lys Asn Ala Gln Leu Asn Ile Glu Gln Asp Val Ala Pro
    450                 455                 460
His
465

<210> SEQ ID NO 5
<211> LENGTH: 1395
<212> TYPE: DNA
<213> ORGANISM: Canis familiaris

<400> SEQUENCE: 5
ccacccaata caagtaaagt ttattcctac tttgaatgcc gtgaaaagaa gacagaaaac      60
tccaaaataa agaaggtgaa atacgaggaa acagtatttt atgggttgca gtacattctt     120
aataagtact taaaggtaa agtagtgacc gcagagaaga tccaggaagc caaagaggtg      180
tatagagagc atttccagga tgatgtcttt aatgaaaagg gatggaacta cattcttgag     240
aaatatgatg gcaccttcc aatagaaata aaagctgttc ctgagggcta tgtcattccc      300
cgaggaaatg ttctcttcac tgtggaaaac acagatccag agtgttactg gcttacaaat     360
tggattgaga ctattcttgt tcagtcctgg tatccaatca gagtagccac aaattctaga     420
gagcaaaaga aaatattggc caaatatttg ttggagacat ctggtaattt ggatggcctg    480
gaatacaagt tacatgattt tggctacaga gggagtttctt cccaagagac tgctggcatc     540
ggagcgtctg ctcatttggt taacttcaaa ggaacagata cagtagcagg aattgctttt    600
gttaaaaaat actatggaac gaaagatcct gttccaggct attctgttcc agcagcagaa     660
cacagtacca atacagcctg ggggaaagac cgtgaaaaag acgcttttga acatatagta     720
acacagtttt catcagtgcc tgtatctgtg gtcagcgata gctatgacat ttacaacgcg     780
tgtgaaaaaa tatggggaga agatctaaga catttaatat tgtcaagaac tacagaggca     840
```

-continued

```
ccactaataa tcagacctga ttctggaaat cctctggaca ctgtattaaa ggttttggat      900
attttgggta agaagttccc tattactgag aactcaaagg gctacaagtt gctgccacct      960
tatcttagag ttattcaagg ggatggagta gatattaata ccttacaaga gattgtagaa     1020
ggcatgaagc aaaaaaaatg gagtattgaa aatattgcct ttggttctgg tggagctttg     1080
ctacagaagt taacaagaga tctcttgaat tgttccttca agtgtagtta tgttgtaacc     1140
aatggccttg ggattaatgt cttcaaggac ccagtcgctg atcccaacaa agatccaaa      1200 aagggtcgat tatctttaca taggacacca gcagggaatt ttgttacact tgaagaagga     1260
aaaggagacc ttgaggaata tggtcatgat cttctcccata ccgtcttcaa gaatgggaag    1320
gtgacaaaaa gctattcatt tgatgaaata agaaaaaatg caaagctgaa tatcgaactg     1380
gaagtagcac ctcat                                                      1395
```

<210> SEQ ID NO 6
<211> LENGTH: 465
<212> TYPE: PRT
<213> ORGANISM: Canis familiaris

<400> SEQUENCE: 6

```
Pro Pro Asn Thr Ser Lys Val Tyr Ser Tyr Phe Glu Cys Arg Glu Lys
1               5                   10                  15

Lys Thr Glu Asn Ser Lys Ile Lys Lys Val Lys Tyr Glu Glu Thr Val
            20                  25                  30

Phe Tyr Gly Leu Gln Tyr Ile Leu Asn Lys Tyr Leu Lys Gly Lys Val
        35                  40                  45

Val Thr Ala Glu Lys Ile Gln Glu Ala Lys Glu Val Tyr Arg Glu His
    50                  55                  60

Phe Gln Asp Asp Val Phe Asn Glu Lys Gly Trp Asn Tyr Ile Leu Glu
65                  70                  75                  80

Lys Tyr Asp Gly His Leu Pro Ile Glu Ile Lys Ala Val Pro Glu Gly
                85                  90                  95

Tyr Val Ile Pro Arg Gly Asn Val Leu Phe Thr Val Glu Asn Thr Asp
            100                 105                 110

Pro Glu Cys Tyr Trp Leu Thr Asn Trp Ile Glu Thr Ile Leu Val Gln
        115                 120                 125

Ser Trp Tyr Pro Ile Thr Val Ala Thr Asn Ser Arg Glu Gln Lys Lys
    130                 135                 140

Ile Leu Ala Lys Tyr Leu Leu Glu Thr Ser Gly Asn Leu Asp Gly Leu
145                 150                 155                 160

Glu Tyr Lys Leu His Asp Phe Gly Tyr Arg Gly Val Ser Ser Gln Glu
                165                 170                 175

Thr Ala Gly Ile Gly Ala Ser Ala His Leu Val Asn Phe Lys Gly Thr
            180                 185                 190

Asp Thr Val Ala Gly Ile Ala Phe Val Lys Lys Tyr Tyr Gly Thr Lys
        195                 200                 205

Asp Pro Val Pro Gly Tyr Ser Val Pro Ala Ala Glu His Ser Thr Ile
    210                 215                 220

Thr Ala Trp Gly Lys Asp Arg Glu Lys Asp Ala Phe Glu His Ile Val
225                 230                 235                 240

Thr Gln Phe Ser Ser Val Pro Val Ser Val Val Ser Asp Ser Tyr Asp
                245                 250                 255

Ile Tyr Asn Ala Cys Glu Lys Ile Trp Gly Glu Asp Leu Arg His Leu
            260                 265                 270
```

```
Ile Leu Ser Arg Thr Thr Glu Ala Pro Leu Ile Ile Arg Pro Asp Ser
        275                 280                 285

Gly Asn Pro Leu Asp Thr Val Leu Lys Val Leu Asp Ile Leu Gly Lys
    290                 295                 300

Lys Phe Pro Ile Thr Glu Asn Ser Lys Gly Tyr Lys Leu Leu Pro Pro
305                 310                 315                 320

Tyr Leu Arg Val Ile Gln Gly Asp Gly Val Asp Ile Asn Thr Leu Gln
                325                 330                 335

Glu Ile Val Glu Gly Met Lys Gln Lys Lys Trp Ser Ile Glu Asn Ile
            340                 345                 350

Ala Phe Gly Ser Gly Gly Ala Leu Leu Gln Lys Leu Thr Arg Asp Leu
        355                 360                 365

Leu Asn Cys Ser Phe Lys Cys Ser Tyr Val Val Thr Asn Gly Leu Gly
    370                 375                 380

Ile Asn Val Phe Lys Asp Pro Val Ala Asp Pro Asn Lys Arg Ser Lys
385                 390                 395                 400

Lys Gly Arg Leu Ser Leu His Arg Thr Pro Ala Gly Asn Phe Val Thr
                405                 410                 415

Leu Glu Glu Gly Lys Gly Asp Leu Glu Glu Tyr Gly His Asp Leu Leu
            420                 425                 430

His Thr Val Phe Lys Asn Gly Lys Val Thr Lys Ser Tyr Ser Phe Asp
        435                 440                 445

Glu Ile Arg Lys Asn Ala Lys Leu Asn Ile Glu Leu Glu Val Ala Pro
    450                 455                 460

His
465

<210> SEQ ID NO 7
<211> LENGTH: 1395
<212> TYPE: DNA
<213> ORGANISM: Equus caballus

<400> SEQUENCE: 7
ccacccaaca caagcaaagt ttattcctac tttgaatgcc gtgaaaagaa gacagaaaat    60
tccaaaataa ggaaggtgaa atacgaggaa acggtatttt atgggttgca gtacattctt   120
aataagtact taaaaggtaa agtagtgacc agagagaaga tccaggaggc caaagaggtg   180
tacagagagc atttccaaga tgacgtcttc aacgagaagg gctggaacta cattcttgag   240
aaatatgatg gcatcttcc aatagaagta aaagctgttc ctgagggctc tgtggttccc   300
agaggaaatg tgctcttcac agtggaaaac acagatccag agtgtttctg gcttacaaat   360
tggattgaga ctattcttgt tcaatcctgg tatccaatca cagtggccac aaattctaga   420
gagcagaaga aatattggc caaatatttg ttagaaacat ctggtaactt agatcgtctg   480
gaatacaagt tacatgattt tggctaccga ggagtctcct cccaagagac tgctggcata   540
ggagcgtccg ctcatttggt taacttcaaa ggaacagata cagtagcagg aattgcttta   600
attaaaaaat actatggaac gaaagatcct gttccaggct attctgttcc agcagcagaa   660
cacagtacca taacagcttg ggggaaagaa catgaaaaag atgcttttga acatatagta   720 acacagttttt catcagtgcc tgtatctgtg gtcagcgata gctatgacat ttataatgcg   780
tgtgagaaaa tatggggtga agacctaaga catttaatag tatcaagaag tacagaggca   840
ccactaataa tcagacctga ttctggaaat cctcttgaca ctgtattaaa ggttttggat   900
attttaggta agaagttccc cgtcactgag aactcaaagg gctacaagtt gctgcctcct   960
```

```
tatcttagag ttattcaagg ggatggagta gatattaaca ccttacaaga gattgtagaa    1020
ggcatgaagc aaaaaaaatg gagtattgaa aatatttcct tcggttctgg tggagctttg    1080
ctacagaaat taacaagaga tctcttgaat tgttccttca agtgtagtta tgttgtaacc    1140
aatggtcttg ggattaatgt ctttaaggac ccagttgctg atcccaacaa aaggtccaaa    1200
aaaggccgat tatctttaca taggacacca gcagggaatt ttgttacact tgaggaagga    1260
aaaggagacc ttgaggaata tgggcatgat cttctccata ctgtcttcaa gaatgggaag    1320
gtgacaaaaa gctattcatt tgatgaagtg agaaaaaatg caaagctgaa tatcgaactg    1380
gaagcagcac cccat                                                    1395
```

<210> SEQ ID NO 8
<211> LENGTH: 465
<212> TYPE: PRT
<213> ORGANISM: Equus caballus

<400> SEQUENCE: 8

```
Pro Pro Asn Thr Ser Lys Val Tyr Ser Tyr Phe Glu Cys Arg Glu Lys
1               5                   10                  15

Lys Thr Glu Asn Ser Lys Ile Arg Lys Val Lys Tyr Glu Glu Thr Val
            20                  25                  30

Phe Tyr Gly Leu Gln Tyr Ile Leu Asn Lys Tyr Leu Lys Gly Lys Val
        35                  40                  45

Val Thr Arg Glu Lys Ile Gln Glu Ala Lys Glu Val Tyr Arg Glu His
    50                  55                  60

Phe Gln Asp Asp Val Phe Asn Glu Lys Gly Trp Asn Tyr Ile Leu Glu
65                  70                  75                  80

Lys Tyr Asp Gly His Leu Pro Ile Glu Val Lys Ala Val Pro Glu Gly
                85                  90                  95

Ser Val Val Pro Arg Gly Asn Val Leu Phe Thr Val Glu Asn Thr Asp
            100                 105                 110

Pro Glu Cys Phe Trp Leu Thr Asn Trp Ile Glu Thr Ile Leu Val Gln
        115                 120                 125

Ser Trp Tyr Pro Ile Thr Val Ala Thr Asn Ser Arg Glu Gln Lys Lys
    130                 135                 140

Ile Leu Ala Lys Tyr Leu Leu Glu Thr Ser Gly Asn Leu Asp Arg Leu
145                 150                 155                 160

Glu Tyr Lys Leu His Asp Phe Gly Tyr Arg Gly Val Ser Ser Gln Glu
                165                 170                 175

Thr Ala Gly Ile Gly Ala Ser Ala His Leu Val Asn Phe Lys Gly Thr
            180                 185                 190

Asp Thr Val Ala Gly Ile Ala Leu Ile Lys Lys Tyr Tyr Gly Thr Lys
        195                 200                 205

Asp Pro Val Pro Gly Tyr Ser Val Pro Ala Ala Glu His Ser Thr Ile
    210                 215                 220

Thr Ala Trp Gly Lys Glu His Glu Lys Asp Ala Phe Glu His Ile Val
225                 230                 235                 240

Thr Gln Phe Ser Ser Val Pro Val Ser Val Ser Asp Ser Tyr Asp
                245                 250                 255

Ile Tyr Asn Ala Cys Glu Lys Ile Trp Gly Glu Asp Leu Arg His Leu
            260                 265                 270

Ile Val Ser Arg Ser Thr Glu Ala Pro Leu Ile Ile Arg Pro Asp Ser
        275                 280                 285
```

-continued

```
Gly Asn Pro Leu Asp Thr Val Leu Lys Val Leu Asp Ile Leu Gly Lys
    290                 295                 300

Lys Phe Pro Val Thr Glu Asn Ser Lys Gly Tyr Lys Leu Leu Pro Pro
305                 310                 315                 320

Tyr Leu Arg Val Ile Gln Gly Asp Gly Val Asp Ile Asn Thr Leu Gln
                325                 330                 335

Glu Ile Val Glu Gly Met Lys Gln Lys Lys Trp Ser Ile Glu Asn Ile
            340                 345                 350

Ser Phe Gly Ser Gly Gly Ala Leu Leu Gln Lys Leu Thr Arg Asp Leu
        355                 360                 365

Leu Asn Cys Ser Phe Lys Cys Ser Tyr Val Val Thr Asn Gly Leu Gly
    370                 375                 380

Ile Asn Val Phe Lys Asp Pro Val Ala Asp Pro Asn Lys Arg Ser Lys
385                 390                 395                 400

Lys Gly Arg Leu Ser Leu His Arg Thr Pro Ala Gly Asn Phe Val Thr
                405                 410                 415

Leu Glu Glu Gly Lys Gly Asp Leu Glu Glu Tyr Gly His Asp Leu Leu
            420                 425                 430

His Thr Val Phe Lys Asn Gly Lys Val Thr Lys Ser Tyr Ser Phe Asp
        435                 440                 445

Glu Val Arg Lys Asn Ala Lys Leu Asn Ile Glu Leu Glu Ala Ala Pro
    450                 455                 460

His
465

<210> SEQ ID NO 9
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
gcacaguacc auaacggcu                                                  19

<210> SEQ ID NO 10
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
agccguuaug guacugugc                                                  19

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11
```

```
gcacaguacc auaacggcut t                                        21

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12
agccguuaug guacugugct t                                        21

<210> SEQ ID NO 13
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ggucuuagau auuuuaggc                                           19

<210> SEQ ID NO 14
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
gccuaaaaua ucuaagacc                                           19

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 15
ggucuuagau auuuuaggct t                                        21

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

```
            Molecule: Synthetic oligonucleotide"

<400> SEQUENCE: 16
gccuaaaaua ucuaagacct t                                              21

<210> SEQ ID NO 17
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
ggcaccacua aucaucaga                                                 19

<210> SEQ ID NO 18
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ucugaugauu aguggugcc                                                 19

<210> SEQ ID NO 19
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ccacccaaca caagcaaagu uuauu                                          25

<210> SEQ ID NO 20
<211> LENGTH: 25
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
aauaaacuuu gcuuguguug ggugg                                          25

<210> SEQ ID NO 21
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ggaaggugaa auaugagga                                                 19

<210> SEQ ID NO 22
<211> LENGTH: 19
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
uccucauauu ucaccuucc                                                  19

<210> SEQ ID NO 23
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
auguucucuu cacggugga                                                  19

<210> SEQ ID NO 24
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
tccaccgtga agagaacat                                                  19

<210> SEQ ID NO 25
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
agggccgauu aucuuuaca                                                  19

<210> SEQ ID NO 26
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
uguaaagaua aucggcccu                                                  19

<210> SEQ ID NO 27
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27
```

```
Phe Ala Arg Lys Gly Ala Leu Arg Gln
1               5

<210> SEQ ID NO 28
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Met Pro Asp Tyr
1
```